(12) United States Patent
Mathieu et al.

(10) Patent No.: US 10,377,825 B2
(45) Date of Patent: Aug. 13, 2019

(54) ANTI-HER2 ANTIBODIES AND METHODS OF USE

(71) Applicant: Genentech, Inc., South San Francisco, CA (US)

(72) Inventors: Mary Mathieu, South San Francisco, CA (US); Mark Dennis, San Carlos, CA (US)

(73) Assignee: Genentech, Inc., South San Francisco, CA (US)

( * ) Notice: Subject to any disclaimer, the term of this patent is extended or adjusted under 35 U.S.C. 154(b) by 55 days.

(21) Appl. No.: 15/842,590

(22) Filed: Dec. 14, 2017

(65) Prior Publication Data

US 2018/0094056 A1 Apr. 5, 2018

Related U.S. Application Data

(63) Continuation of application No. PCT/US2016/037891, filed on Jun. 16, 2016.

(60) Provisional application No. 62/181,106, filed on Jun. 17, 2015.

(51) Int. Cl.
| | | |
|---|---|---|
| *A61K 39/395* | (2006.01) | |
| *C07K 16/28* | (2006.01) | |
| *C07K 16/32* | (2006.01) | |
| *A61P 35/00* | (2006.01) | |

(52) U.S. Cl.
CPC .... *C07K 16/2809* (2013.01); *A61K 39/39558* (2013.01); *A61P 35/00* (2018.01); *C07K 16/32* (2013.01); *C07K 2317/24* (2013.01); *C07K 2317/31* (2013.01); *C07K 2317/73* (2013.01); *C07K 2317/74* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | |
|---|---|---|
| 5,821,337 A | 10/1998 | Carter et al. |
| 6,733,752 B1 | 5/2004 | Greene et al. |
| 2004/0043446 A1* | 3/2004 | DeFrees .............. C07K 1/006 435/68.1 |
| 2017/0029529 A1 | 2/2017 | Croasdale-Wood et al. |

FOREIGN PATENT DOCUMENTS

| | | | |
|---|---|---|---|
| EP | 2482212 | | 6/2012 |
| WO | 03/087131 | A2 | 10/2003 |
| WO | 2012075581 | | 6/2012 |
| WO | 2012/143524 | A2 | 10/2012 |
| WO | 2015/095392 | | 6/2015 |
| WO | WO2015091738 | * | 6/2015 |

OTHER PUBLICATIONS

Atwell et al., "Stable Heterodimers from Remodeling the Domain Interface of a Homodimer using a Phage Dispaly Library" Journal of Mol. Biol. 270:26-35 ( 1997).
Bostrom et al., "High affinity antigen recognition of the dual specific variants of Herceptin is entropy-driven in spite of structural plasticity" PLoS One 6:e17887 ( 2011).
Carter et al., "Humanization of an anti-p185 HER2 antibody for human cancer therapy" P Natl Acad Sci USA 89:4285-4289 (May 1992).
Drebin et al., "Down-Modulation of an Oncogene Protein Product and Reversion of the Transformed Phenotype by Monoclonal Antibodies" Cell 41(3):695-706 (Jul. 1985).
Gerstner et al., "Sequence Plasticity in the Antigen-binding Site of a Therapeutic Anti-HER2 Antibody" J Mol Biol 321:851-862 ( 2002).
Harris et al., "Identification of multiple sources of charge heterogeneity in a recombinant antibody" J Chromatography B Biomedical Sciences Applications 752(2):233-245 (Mar. 10, 2001).
Huang et al., "In Vivo Deamidation Characterization of Monoclonal Antibody by LC/MS/MS" Anal.Chem. 77:1432-1439 ( 2005).
Junttila et al., "Antitumor Efficacy of a Bispecific Antibody That Targets HER2 and Activates T Cells" Cancer Res 74(19) ( 2014).
Kelley et al., "Antigen binding thermodynamics and antiproliferative effects of chimeric and humanized anti-p185HER2 antibody Fab fragments" Biochem 31:5434-5441 ( 1992).
Kelley et al., "Thermodynamic analysis of an antibody functional epitope" Biochem 32:6828-6835 ( 1993).
Spiess et al., "Bispecific antibodies with natural architecture produced by co-culture of bacteria expressing two distinct half-antibodies" Nature Biotechnology 31(8):753-758 (Aug. 2013).
Yan et al., "Succinimide formation at Asn 55 in the complementarity determing region of a recombinant monoclonal antibody IgG1 heavy chain" J. Pharm. Sci. 98(10):3509-3521 ( 2009).
Yang et al., "Improving Trastuzumab's Stability Profile by Removing the Two Degradation Hotspots" J Pharm Sci 104(6):1960-1970 ( 2015).

* cited by examiner

*Primary Examiner* — Laura B Goddard

(57) ABSTRACT

The invention provides anti-HER2 antibodies, including anti-HER2 antibodies of improved stability or affinity, and methods of using the same.

35 Claims, 6 Drawing Sheets

Specification includes a Sequence Listing.

FIG. 1   Alignment of hu4D5, positions varied (X1-X6) and 4D5v3 sequence

| 4D5 | LC (X1,X2) | CDRH2 (X3,X4) | CDRH3 (X5,X6) | KD (nM) |
|---|---|---|---|---|
| WT | wt | wt | wt | 0.5 |
| Fab1 | ST | NA | DS | .06 |
| Fab2 | WT | NA | WT | .07 |
| Fab3 | WT | NA | TG | .07 |
| Fab4 | WT | EG | DS | .09 |
| Fab5 | WT | EG | DS | 0.6 |
| Fab6 | ST | NA | WT | .82 |
| Fab7 | ST | WT | EG | 1.5 |
| Fab8 | DT | EG | WT | 2.0 |
| Fab9 | DT | EG | DS | 2.3 |
| Fab10 | ND | NA | EG | 12 |
| Fab11 | ND | WT | EG | 14 |
| Fab12 | QT | AG | DS | 19 |
| Fab14 | ND | AG | WT | 27 |
| Fab15 | TT | SG | SG | 27 |
| Fab16 | TT | SG | DT | 32 |
| Fab17 | ET | SG | WT | 36 |
| Fab18 | ET | WT | EG | 87 |
| Fab20 | ND | AG | DS | 88 |
| Fab21 | ET | AG | DS | 200 |
| Fab22 | ET | AG | DS | 400 |

*FIG. 2*

| 4D5 version | Human Her2 KD (nM) |
|---|---|
| 4D5 Fab | 0.3 |
| 4D5 TDB | 0.3 |
| 4D5v3 TDB | .04 |
| 4D5v3 bivalent Mab | .02 |

FIG. 3

HER2 Variant TDB Biacore affinity summary

| 4D5 TDB | L1 | H2 | H3 | KD (nM) |
|---|---|---|---|---|
| wt | NT | NG | DG | 0.5 |
| v1 | DT | EG | DS | 2.0 |
| v2 | ST | EG | TG | 0.6 |
| v3 | ST | NA | TG | 0.06 |
| v4 | ST | wt | DS | 1.0 |
| wt repeat | | | | 0.3 |
| v20 | TT | NA | TG | 0.2 |
| v21 | ST | wt | TG | .04 |
| v22 | ST | wt | EG | .03 |
| v23 | DT | NA | TG | 0.8 |
| v24 | TT | wt | TG | 0.2 |

FIG. 4

ANTI-HER2 ANTIBODIES AND METHODS OF USE

CROSS REFERENCE TO RELATED APPLICATIONS

This application is a continuation of International Application PCT/US16/37891, filed Jun. 16, 2016, which claims the benefit of priority to U.S. Patent Application No. 62/181,106 filed Jun. 17, 2015, the disclosures of both which are is-incorporated herein by reference in their entirety.

SEQUENCE LISTING

The instant application contains a Sequence Listing which has been submitted electronically in ASCII format and is hereby incorporated by reference in its entirety. Said ASCII copy, created on Dec. 12, 2017, is named P32917US_US_ST25.txt and is 71,994 bytes in size.

FIELD OF THE INVENTION

The present invention relates to anti-HER2 antibodies and methods of using the same.

BACKGROUND

Members of the ErbB family of receptor tyrosine kinases are important mediators of cell growth, differentiation and survival. The receptor family includes four distinct members, including epidermal growth factor receptor (EGFR or ErbB1), HER2 (ErbB2 or p185.sup.neu), HER3 (ErbB3) and HER4 (ErbB4 or tyro2).

Antibodies directed against the rat p185$^{neu}$ neu and human ErbB2 protein products have been described. See, for example, Drebin et al., Cell, 41:695-706 (1985); Myers et al., Meth. Enzym. 198:277-290 (1991); and WO94/22478; Tagliabue et al. Int. J. Cancer 47:933-937 (1991); McKenzie et al. Oncogene 4:543-548 (1989); Maier et al. Cancer Res. 51:5361-5369 (1991); Bacus et al. Molecular Carcinogenesis 3:350-362 (1990); Stancovski et al. PNAS (USA) 88:8691-8695 (1991); Bacus et al. Cancer Research 52:2580-2589 (1992); Xu et al. Int. J. Cancer 53:401-408 (1993); WO94/00136; Kasprzyk et al. Cancer Research 52:2771-2776 (1992); Hancock et al. Cancer Res. 51:4575-4580 (1991); Shawver et al. Cancer Res. 54:1367-1373 (1994); Arteaga et al. Cancer Res. 54:3758-3765 (1994); Harwerth et al. J. Biol. Chem. 267:15160-15167 (1992); U.S. Pat. No. 5,783,186; and Klapper et al. Oncogene 14:2099-2109 (1997); Lewis et al. Cancer Research 56:1457-1465 (1996); and Schaefer et al. Oncogene 15:1385-1394 (1997).

The murine monoclonal anti-HER2 antibody 4D5 inhibits the growth of breast cancer cell lines that overexpress HER2 (Lewis et al., Cancer Immunol. Immunother. [1993]). Based on this observation, antibody 4D5 was humanized (Carter et al., Proc. Natl. Acad. Sci. USA 89: 4285-4289 [1992]). The humanized (4D5) monoclonal antibody (hu4D5) is commercially known as the drug Herceptin® (trastuzumab, rhuMAb HER2, U.S. Pat. No. 5,821,337), which gained FDA marketing approval in late 1998. However, there remains a need for improved cancer therapeutics that target cancers expressing the HER2 target antigen.

SUMMARY

The present invention relates to variants of humanized anti-HER2 antibody hu4D5. In some embodiments, the variants have improved stability as compared to hu4D5. In some embodiments, the variants have increased affinity for the Her2 antigen as compared to hu4D5.

One aspect of the invention provides for an isolated anti-HER2 antibody comprising a light chain variable domain (VL) comprising the amino acid sequence of SEQ ID NO: 3 and a heavy chain variable domain (VH) comprising the amino acid sequence of SEQ ID NO: 4. One aspect of the invention provides for an isolated anti-HER2 antibody comprising a light chain variable domain (VL) comprising the amino acid sequence of SEQ ID NO: 3 and a heavy chain variable domain (VH) comprising the amino acid sequence of SEQ ID NO: 5. One aspect of the invention provides for an isolated anti-HER2 antibody comprising a light chain variable domain (VL) and comprising a heavy chain variable domain (VH) comprising the amino acid sequence of SEQ ID NO: 5. One aspect of the invention provides for an isolated anti-HER2 antibody comprising a light chain variable domain (VL) comprising the amino acid sequence of SEQ ID NO: 1 and comprising a heavy chain variable domain (VH) comprising the amino acid sequence of SEQ ID NO: 5.

One aspect of the invention provides for an isolated anti-HER2 antibody comprising a HER2 binding domain comprising (a) an HVR-H1 comprising the amino acid sequence of SEQ ID NO:50; (b) an HVR-H2 comprising the amino acid sequence of SEQ ID NO:57; (c) an HVR-H3 comprising the amino acid sequence of SEQ ID NO:62; (d) an HVR-L1 comprising the amino acid sequence of SEQ ID NO: 53; (e) an HVR-L2 comprising the amino acid sequence of SEQ ID NO:48; and (f) an HVR-L3 comprising the amino acid sequence of SEQ ID NO:49. One aspect of the invention provides for an isolated anti-HER2 antibody comprising a HER2 binding domain: (a) an HVR-H1 comprising the amino acid sequence of SEQ ID NO:50; (b) an HVR-H2 comprising the amino acid sequence of SEQ ID NO:57; (c) an HVR-H3 comprising the amino acid sequence of SEQ ID NO:63; (d) an HVR-L1 comprising the amino acid sequence of SEQ ID NO: 54; (e) an HVR-L2 comprising the amino acid sequence of SEQ ID NO:48; and (f) an HVR-L3 comprising the amino acid sequence of SEQ ID NO:49. One aspect of the invention provides for an isolated anti-HER2 antibody comprising a HER2 binding domain comprising (a) an HVR-H1 comprising the amino acid sequence of SEQ ID NO:50; (b) an HVR-H2 comprising the amino acid sequence of SEQ ID NO:58; (c) an HVR-H3 comprising the amino acid sequence of SEQ ID NO:63; (d) an HVR-L1 comprising the amino acid sequence of SEQ ID NO: 54; (e) an HVR-L2 comprising the amino acid sequence of SEQ ID NO:48; and (f) an HVR-L3 comprising the amino acid sequence of SEQ ID NO:49.

One aspect of the invention provides for an isolated anti-HER2 antibody comprising a HER2 binding domain comprising: (a) an HVR-H1 comprising the amino acid sequence of SEQ ID NO:50; (b) an HVR-H2 comprising the amino acid sequence of SEQ ID NO:51; (c) an HVR-H3 comprising the amino acid sequence of SEQ ID NO:62; (d) an HVR-L1 comprising the amino acid sequence of SEQ ID NO: 54; (e) an HVR-L2 comprising the amino acid sequence of SEQ ID NO:48; and (f) an HVR-L3 comprising the amino acid sequence of SEQ ID NO:49. One aspect of the invention provides for an isolated anti-HER2 antibody comprising a HER2 binding domain comprising (a) an HVR-H1 comprising the amino acid sequence of SEQ ID NO:50; (b) an HVR-H2 comprising the amino acid sequence of SEQ ID NO:58; (c) an HVR-H3 comprising the amino acid sequence of SEQ ID NO:63; (d) an HVR-L1 comprising the amino acid sequence of SEQ ID NO: 55; (e) an HVR-L2 comprising the amino acid sequence of SEQ ID NO:48; and (f) an HVR-L3 comprising the amino acid sequence of SEQ ID NO:49. One aspect of the invention provides for an isolated anti-HER2 antibody comprising a HER2 binding domain comprising: (a) an HVR-H1 comprising the amino acid sequence of SEQ ID NO:50; (b) an HVR-H2 comprising the amino acid sequence of SEQ ID NO:51; (c) an HVR-H3 comprising the amino acid sequence of SEQ ID NO:63; (d) an HVR-L1 comprising the amino acid sequence of SEQ ID NO: 54; (e) an HVR-L2 comprising the amino acid sequence of SEQ ID NO:48; and (f) an HVR-L3 comprising the amino acid sequence of SEQ ID NO:49. One aspect of the invention provides for an isolated anti-HER2 antibody comprising a HER2 binding domain comprising: (a) an HVR-H1 comprising the amino acid sequence of SEQ ID NO:50; (b) an HVR-H2 comprising the amino acid sequence of SEQ ID NO:51; (c) an HVR-H3 comprising the amino acid sequence of SEQ ID NO:65; (d) an HVR-L1 comprising the amino acid sequence of SEQ ID NO:54; (e) an HVR-L2 comprising the amino acid sequence of SEQ ID NO:48; and (f) an HVR-L3 comprising the amino acid sequence of SEQ ID NO:49.

One aspect of the invention provides for an isolated anti-HER2 antibody comprising a HER2 binding domain comprising: (a) an HVR-H1 comprising the amino acid sequence of SEQ ID NO:50; (b) an HVR-H2 comprising the amino acid sequence of SEQ ID NO:58; (c) an HVR-H3 comprising the amino acid sequence of SEQ ID NO:63; (d) an HVR-L1 comprising the amino acid sequence of SEQ ID NO:53; (e) an HVR-L2 comprising the amino acid sequence of SEQ ID NO:48; and (f) an HVR-L3 comprising the amino acid sequence of SEQ ID NO:49. One aspect of the invention provides for an isolated anti-HER2 antibody comprising a HER2 binding domain comprising: (a) an HVR-H1 comprising the amino acid sequence of SEQ ID NO:50; (b) an HVR-H2 comprising the amino acid sequence of SEQ ID NO:51; (c) an HVR-H3 comprising the amino acid sequence of SEQ ID NO:63; (d) an HVR-L1 comprising the amino acid sequence of SEQ ID NO:55; (e) an HVR-L2 comprising the amino acid sequence of SEQ ID NO:48; and (f) an HVR-L3 comprising the amino acid sequence of SEQ ID NO:49.

One aspect of the invention provides for an isolated anti-HER2 antibody comprising a HER2 binding domain comprising a light chain variable domain (VL) comprising the amino acid sequence of SEQ ID NO: 6 and a heavy chain variable domain (VH) comprising the amino acid sequence of SEQ ID NO: 7. One aspect of the invention provides for an isolated anti-HER2 antibody comprising a HER2 binding domain comprising a light chain variable domain (VL) comprising the amino acid sequence of SEQ ID NO: 8 and a heavy chain variable domain (VH) comprising the amino acid sequence of SEQ ID NO: 9. One aspect of the invention provides for an isolated anti-HER2 antibody comprising a HER2 binding domain comprising a light chain variable domain (VL) comprising the amino acid sequence of SEQ ID NO: 10 and a heavy chain variable domain (VH) comprising the amino acid sequence of SEQ ID NO: 11. One aspect of the invention provides for an isolated anti-HER2 antibody comprising a HER2 binding domain comprising a light chain variable domain (VL) comprising the amino acid sequence of SEQ ID NO: 12 and a heavy chain variable domain (VH) comprising the amino acid sequence of SEQ ID NO: 13. One aspect of the invention provides for an isolated anti-HER2 antibody comprising a HER2 binding domain comprising a light chain variable domain (VL) comprising the amino acid sequence of SEQ ID NO: 14 and a heavy chain variable domain (VH) comprising the amino acid sequence of SEQ ID NO: 15. One aspect of the invention provides for an isolated anti-HER2 antibody comprising a HER2 binding domain comprising a light chain variable domain (VL) comprising the amino acid sequence of SEQ ID NO: 16 and a heavy chain variable domain (VH) comprising the amino acid sequence of SEQ ID NO: 17. One aspect of the invention provides for an isolated anti-HER2 antibody comprising a HER2 binding domain comprising a light chain variable domain (VL) comprising the amino acid sequence of SEQ ID NO: 18 and a heavy chain variable domain (VH) comprising the amino acid sequence of SEQ ID NO: 19. One aspect of the invention provides for an isolated anti-HER2 antibody comprising a HER2 binding domain comprising a light chain variable domain (VL) comprising the amino acid sequence of SEQ ID NO: 20 and a heavy chain variable domain (VH) comprising the amino acid sequence of SEQ ID NO: 21. One aspect of the invention provides for an isolated anti-HER2 antibody comprising a HER2 binding domain comprising a light chain variable domain (VL) comprising the amino acid sequence of SEQ ID NO: 22 and a heavy chain variable domain (VH) comprising the amino acid sequence of SEQ ID NO: 23.

One aspect of the invention provides for an isolated anti-HER2 antibody of any of the preceeding aspects, wherein the anti-HER2 antibody further comprising an anti-CD3 binding domain. In one embodiment, the anti-CD3 binding domain comprises (a) HVR-H1 comprising the amino acid sequence of SEQ ID NO:84 (b) HVR-H2 comprising the amino acid sequence of SEQ ID NO:85; (c) HVR-H3 comprising the amino acid sequence of SEQ ID NO:86; (d) HVR-L1 comprising the amino acid sequence of SEQ ID NO:69; (e) HVR-L2 comprising the amino acid sequence of SEQ ID NO:87, and (f) HVR-L3 comprising the amino acid sequence of SEQ ID NO:88. In one embodiment, the anti-CD3 binding domain comprises (a) HVR-H1 comprising the amino acid sequence of SEQ ID NO:66; (b) HVR-H2 comprising the amino acid sequence of SEQ ID NO:67; (c) HVR-H3 comprising the amino acid sequence of SEQ ID NO:68; (d) HVR-L1 comprising the amino acid sequence of SEQ ID NO:69; (e) HVR-L2 comprising the amino acid sequence of SEQ ID NO:70, and (f) HVR-L3 comprising the amino acid sequence of SEQ ID NO:71. In one embodiment, the anti-CD3 binding domain comprises a VH domain comprising the amino acid sequence of SEQ ID NO:77 and a VL domain comprising the amino acid sequence of SEQ ID NO:78. In one embodiment, the anti-CD3 binding domain comprises (a) HVR-H1 comprising the amino acid sequence of SEQ ID NO:72; (b) HVR-H2 comprising the amino acid sequence of SEQ ID NO:73; (c) HVR-H3 comprising the amino acid sequence of SEQ ID NO:74; (d) HVR-L1 comprising the amino acid sequence of SEQ ID NO:69; (e) HVR-L2 comprising the amino acid sequence of SEQ ID NO:75; and (f) HVR-L3 comprising the amino acid sequence of SEQ ID NO:76. In one embodiment, the anti-CD3 binding domain comprises comprises a VH domain comprising the amino acid sequence of SEQ ID NO:79 and a VL domain comprising the amino acid sequence of SEQ ID NO:81.

In certain embodiments of the above aspects, the anti-HER2 antibody is a monoclonal, human, humanized, or chimeric antibody. In certain embodiments of the above aspects, the anti-HER2 antibody is an IgG antibody. In certain embodiments of the above aspects, the anti-HER2 antibody is a multispecific antibody. In certain embodiments of the above aspects, the anti-HER2 antibody is a full-length antibody. In certain embodiments of the above aspects, the anti-HER2 antibody comprises an aglycosylation site mutation. In certain embodiments of the above aspects, the anti-HER2 antibody comprises an aglycosylation site mutation that is a substitution mutation. In certain embodiments of the above aspects, the anti-HER2 antibody has reduced effector function. In certain embodiments of the above aspects, the anti-HER2 antibody comprises a substitution mutation is at amino acid residue N297, L234, L235, D265, and/or P329G according to EU numbering. In certain the substitution mutation is selected from the group consisting of N297G, N297A, L234A, L235A, D265A, and P329G according to EU numbering. In certain embodiments of the above aspects, the anti-HER2 antibody comprises an N297G substitution mutation at amino acid residue 297 according to EU numbering.

In certain embodiments of the above aspects, the anti-HER2 antibody is an antibody fragment, such as a Fab, Fab'-SH, Fv, scFv, and/or (Fab')2 fragment.

One aspect of the invention provides an isolated nucleic acid encoding the anti-HER2 antibody of any of the above aspects. One aspect of the invention provides a vector comprising the isolated nucleic acid. One aspect of the invention provides a host cell comprising the vector.

One aspect of the invention provides a method of producing the anti-HER2 antibody, the method comprising culturing the host cell in a culture medium.

One aspect of the invention provides a pharmaceutical composition comprising the anti-HER2 antibody of any of the above aspects. One aspect of the invention provides an anti-HER2 antibody of any of the above aspects for use as a medicament. The medicament finds use in treating or delaying progression of a cell proliferative disorder in a subject in need thereof. One aspect of the invention provides an anti-HER2 antibody of any of the above aspects for use in enhancing immune function in a subject having a cell proliferative disorder, such cancer. In certain embodiments, the cancer is a cancer which expresses HER2. In one embodiment, the cancer is is a HER2 positive cancer. In some embodiments, the cancer is breast cancer or gastric cancer.

One aspect of the invention provides for use of the anti-HER2 antibody of any of the above aspects in the manufacture of a medicament for treating or delaying progression of a cell proliferative disorder, such as cancer. In certain embodiments, the cancer is a cancer which expresses HER2. In one embodiment, the cancer is is a HER2 positive cancer. In some embodiments, the cancer is breast cancer or gastric cancer.

One aspect of the invention provides a method of treating or delaying the progression of a cell proliferative disorder in a subject in need thereof, the method comprising administering to the subject the anti-HER2 antibody of any of the above aspects.

One aspect of the invention provides method of enhancing immune function in a subject having a cell proliferative disorder, the method comprising administering to the subject an effective amount of the anti-HER2 antibody of any of the above aspects. In certain embodiments, the cell proliferative disorder is a cancer. In certain embodiments, the cancer is a cancer which expresses HER2. In one embodiment, the cancer is is a HER2 positive cancer. In some embodiments, the cancer is breast cancer or gastric cancer. In certain embodiments, the method further comprises administering to the subject a PD-1 axis binding antagonist (such as an anti-PDL1 antibody).

BRIEF DESCRIPTION OF THE DRAWINGS

FIG. 1 shows the amino acid sequence alignment of hu4D5 (Herceptin®), hu4D5 with substituted amino acid positions (X1-X6) shaded, and variant 4D5v3 (SEQ ID NOS 1, 3, 10, 2, 4 and 11, respectively, in order of appearance).

FIG. 2 is a table summarizing monovalent binding affinities for Fab versions of the anti-HER2 variants as determined by surface plasmon resonance.

FIG. 3 is a table summarizing the binding affinities of select anti-HER2 antibodies as determined by surface plasmon resonance.

FIG. 4 is a table summarizing the binding affinities of select anti-HER2/CD3 bispecific antibodies as determined by surface plasmon resonance.

DETAILED DESCRIPTION OF EMBODIMENTS OF THE INVENTION

I. Definitions

Figure 5A:
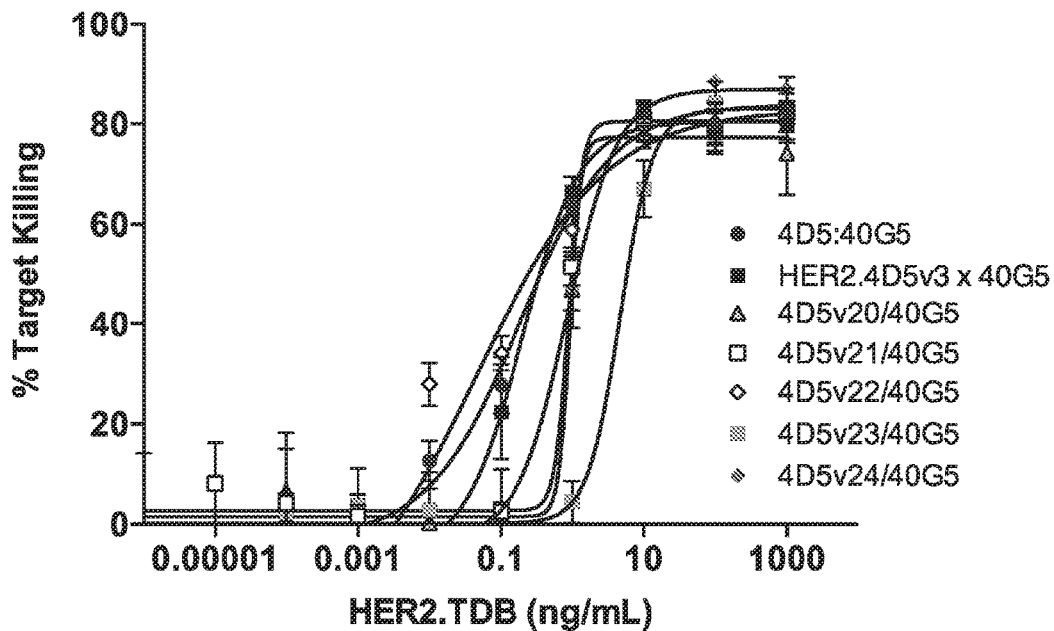
FIGS. 5A-C depicts cell killing assays performed to evaluate the functional activity of the anti-HER2/CD3 TDBs using purified human CD8+ cells and a HER2 expressing target cell line.

The term "about" as used herein refers to the usual error range for the respective value readily known to the skilled person in this technical field. Reference to "about" a value or parameter herein includes (and describes) embodiments that are directed to that value or parameter per se.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following. An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-CD3 antibody" and "an antibody that binds to CD3" refer to an antibody that is capable of binding CD3 with sufficient affinity such that the antibody is useful as a diagnostic and/or therapeutic agent in targeting CD3. In one embodiment, the extent of binding of an anti-CD3 antibody to an unrelated, non-CD3 protein is less than about 10% of the binding of the antibody to CD3 as measured, e.g., by a radioimmunoassay (RIA). In certain embodiments, an antibody that binds to CD3 has a dissociation constant (Kd) of ≤1 µM, ≤100 nM, ≤10 nM, ≤1 nM, ≤0.1 nM, ≤0.01 nM, or ≤0.001 nM (e.g. $10^{-8}$M or less, e.g. from $10^{-8}$M to $10^{-13}$M, e.g., from $10^{-9}$M to $10^{-13}$ M). In certain embodiments, an anti-CD3 antibody binds to an epitope of CD3 that is conserved among CD3 from different species.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

By "binding domain" is meant a part of a compound or a molecule that specifically binds to a target epitope, antigen, ligand, or receptor. Binding domains include but are not limited to antibodies (e.g., monoclonal, polyclonal, recombinant, humanized, and chimeric antibodies), antibody fragments or portions thereof (e.g., Fab fragments, Fab'2, scFv antibodies, SMIP, domain antibodies, diabodies, minibodies, scFv-Fc, affibodies, nanobodies, and VH and/or VL domains of antibodies), receptors, ligands, aptamers, and other molecules having an identified binding partner.

A "chemotherapeutic agent" is a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega II (see, e.g., Nicolaou et al., *Angew. Chem Intl. Ed. Engl.*, 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); combretastatin; folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2'-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®, Bristol-Myers Squibb Oncology, Princeton, N.J.), albumin-engineered nanoparticle formulation of paclitaxel (ABRAXANE™) and docetaxel (TAXOTERE®, Rhome-Poulene Rorer, Antony, France); chloranbucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylornithine (DMF®); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R) (e.g., erlotinib (Tarceva™)); and VEGF-A that reduce cell proliferation; vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (sunitinib, SUTENT®, Pfizer); perifosine, COX-2 inhibitor (e.g. celecoxib or etoricoxib), proteosome inhibitor (e.g. PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors; tyrosine kinase inhibitors; serine-threonine kinase inhibitors such as rapamycin (sirolimus, RAPAMUNE®); farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin, and pharmaceutically acceptable salts, acids or derivatives of any of the above; as well as combinations of two or more of the above.

Chemotherapeutic agents as defined herein include "antihormonal agents" or "endocrine therapeutics" which act to regulate, reduce, block, or inhibit the effects of hormones that can promote the growth of cancer. They may be hormones themselves, including, but not limited to: antiestrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON.cndot.toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in aberrant cell proliferation, such as, for example, PKC-alpha, Raf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; Vinorelbine and Esperamicins (see U.S. Pat. No. 4,675,187), and pharmaceutically acceptable salts, acids or derivatives of any of the above; as well as combinations of two or more of the above.

The term "chimeric" antibody refers to an antibody in which a portion of the heavy and/or light chain is derived from a particular source or species, while the remainder of the heavy and/or light chain is derived from a different source or species.

The term "cluster of differentiation 3" or "CD3," as used herein, refers to any native CD3 from any vertebrate source, including mammals such as primates (e.g. humans) and rodents (e.g., mice and rats), unless otherwise indicated, including, for example, CD3ε, CD3γ, CD3α, and CD3β chains. The term encompasses "full-length," unprocessed CD3 (e.g., unprocessed or unmodified CD3ε or CD3γ), as well as any form of CD3 that results from processing in the cell. The term also encompasses naturally occurring variants of CD3, including, for example, splice variants or allelic variants. CD3 includes, for example, human CD3ε protein (NCBI RefSeq No. NP_000724), which is 207 amino acids in length, and human CD3γ protein (NCBI RefSeq No. NP_000064), which is 182 amino acids in length.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

It is understood that aspects and embodiments of the invention described herein include "comprising," "consisting," and "consisting essentially of" aspects and embodiments.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

A "disorder" is any condition that would benefit from treatment including, but not limited to, chronic and acute disorders or diseases including those pathological conditions which predispose the mammal to the disorder in question.

The terms "cell proliferative disorder" and "proliferative disorder" refer to disorders that are associated with some degree of abnormal cell proliferation. In one embodiment, the cell proliferative disorder is cancer. In one embodiment, the cell proliferative disorder is a tumor.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia or lymphoid malignancies. More particular examples of such cancers include, but not limited to, squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer and gastrointestinal stromal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, superficial spreading melanoma, lentigo maligna melanoma, acral lentiginous melanomas, nodular melanomas, multiple myeloma and B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); hairy cell leukemia; chronic myeloblastic leukemia; and post-transplant lymphoproliferative disorder (PTLD), as well as abnormal vascular proliferation associated with phakomatoses, edema (such as that associated with brain tumors), Meigs' syndrome, brain, as well as head and neck cancer, and associated metastases. In certain embodiments, cancers that are amenable to treatment by the antibodies of the invention include breast cancer, colorectal cancer, rectal cancer, non-small cell lung cancer, glioblastoma, non-Hodgkins lymphoma (NHL), renal cell cancer, prostate cancer, liver cancer, pancreatic cancer, soft-tissue sarcoma, kaposi's sarcoma, carcinoid carcinoma, head and neck cancer, ovarian cancer, mesothelioma, and multiple myeloma. In some embodiments, the cancer is selected from: small cell lung cancer, gliblastoma, neuroblastomas, melanoma, breast carcinoma, gastric cancer, colorectal cancer (CRC), and hepatocellular carcinoma. Yet, in some embodiments, the cancer is selected from: non-small cell lung cancer, colorectal cancer, glioblastoma and breast carcinoma, including metastatic forms of those cancers. In other embodiments, the cancer is selected from a class of mature B-Cell cancers excluding Hodgkin's Lymphoma but including germinal-center B-cell-like (GCB) DLBCL, activated B-cell-like (ABC) DLBCL, follicular lymphoma (FL), mantle cell lymphoma (MCL), acute myeloid leukemia (AML), chronic lymphoid leukemia (CLL), marginal zone lymphoma (MZL), small lymphocytic leukemia (SLL), lymphoplasmacytic lymphoma (LL), Waldenstrom macroglobulinemia (WM), central nervous system lymphoma (CNSL), Burkitt's lymphoma (BL), B-cell prolymphocytic leukemia, Splenic marginal zone lymphoma, Hairy cell leukemia, Splenic lymphoma/leukemia, unclassifiable, Splenic diffuse red pulp small B-cell lymphoma, Hairy cell leukemia variant, Waldenström macroglobulinemia, Heavy chain diseases, a Heavy chain disease, γ Heavy chain disease, p Heavy chain disease, Plasma cell myeloma, Solitary plasmacytoma of bone, Extraosseous plasmacytoma, Extranodal marginal zone lymphoma of mucosa-associated lymphoid tissue (MALT lymphoma), Nodal marginal zone lymphoma, Pediatric nodal marginal zone lymphoma, Pediatric follicular lymphoma, Primary cutaneous follicle centre lymphoma, T-cell/histiocyte rich large B-cell lymphoma, Primary DLBCL of the CNS, Primary cutaneous DLBCL, leg type, EBV-positive DLBCL of the elderly, DLBCL associated with chronic inflammation, Lymphomatoid granulomatosis, Primary mediastinal (thymic) large B-cell lymphoma, Intravascular large B-cell lymphoma, ALK-positive large B-cell lymphoma, Plasmablastic lymphoma, Large B-cell lymphoma arising in HHV8-associated multicentric Castleman disease, Primary effusion lymphoma: B-cell lymphoma, unclassifiable, with features intermediate between diffuse large B-cell lymphoma and Burkitt lymphoma, and B-cell lymphoma, unclassifiable, with features intermediate between diffuse large B-cell lymphoma and classical Hodgkin lymphoma.

"Tumor," as used herein, refers to all neoplastic cell growth and proliferation, whether malignant or benign, and all pre-cancerous and cancerous cells and tissues. The terms "cancer", "cancerous", "cell proliferative disorder", "proliferative disorder" and "tumor" are not mutually exclusive as referred to herein.

The term "tumor antigen," as used herein, may be understood as those antigens that are presented on tumor cells. These antigens can be presented on the cell surface with an extracellular part, which is often combined with a trans-membrane and cytoplasmic part of the molecule. These antigens can sometimes be presented only by tumor cells and never by the normal ones. Tumor antigens can be exclusively expressed on tumor cells or might represent a tumor specific mutation compared to normal cells. In this case, they are called tumor-specific antigens. More common are tumor antigens that are presented by tumor cells and normal cells, and they are called tumor-associated antigens. These tumor-associated antigens can be overexpressed compared to normal cells or are accessible for antibody binding in tumor cells due to the less compact structure of the tumor tissue compared to normal tissue. In one aspect the tumor antigen is selected from those set forth in Table 1 below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of a compound, for example, an anti-HER2 antibody of the invention or a composition (e.g., pharmaceutical composition) thereof, is at least the minimum amount required to achieve the desired therapeutic or prophylactic result, such as a measurable improvement or prevention of a particular disorder (e.g., a cell proliferative disorder, e.g., cancer). An effective amount herein may vary according to factors such as the disease state, age, sex, and weight of the patient, and the ability of the antibody to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In the case of cancer or tumor, an effective amount of the drug may have the effect in reducing the number of cancer cells; reducing the tumor size; inhibiting (i.e., slow to some extent or desirably stop) cancer cell infiltration into peripheral organs; inhibit (i.e., slow to some extent and desirably stop) tumor metastasis; inhibiting to some extent tumor growth; and/or relieving to some extent one or more of the symptoms associated with the disorder. An effective amount can be administered in one or more administrations. For purposes of this invention, an effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full-length antibody," "intact antibody," and "whole antibody" are used herein interchangeably to refer to an antibody having a structure substantially similar to a native antibody structure or having heavy chains that contain an Fc region as defined herein.

A "growth inhibitory agent" when used herein refers to a compound or composition which inhibits growth of a cell either in vitro or in vivo. In one embodiment, growth inhibitory agent is growth inhibitory antibody that prevents or reduces proliferation of a cell expressing an antigen to which the antibody binds. In another embodiment, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in Mendelsohn and Israel, eds., The Molecular Basis of Cancer, Chapter 1, entitled "Cell cycle regulation, oncogenes, and antineoplastic drugs" by Murakami et al. (W.B. Saunders, Philadelphia, 1995), e.g., p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

The term "HER2-positive" cancer comprises cancer cells which have higher than normal levels of HER2. Examples of HER2-positive cancer include HER2-positive breast cancer and HER2-positive gastric cancer. Optionally, HER2-positive cancer has an immunohistochemistry (IHC) score of 2+ or 3+ and/or an in situ hybridization (ISH) amplification ratio 2.0.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.*, 227:381 (1991); Marks et al., *J. Mol. Biol.*, 222:581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.*, 147(1):86-95 (1991). See also van Dijk and van de Winkel, *Curr. Opin. Pharmacol.*, 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Natl. Acad. Sci. USA*, 103:3557-3562 (2006) regarding human antibodies generated via a human B-cell hybridoma technology.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest,* 5th Ed. Public Health Service, National Institutes of Health, Bethesda, Md. (1991));

(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

A "subject" or an "individual" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the subject or individual is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-HER2 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

The term "PD-1 axis binding antagonist" refers to a molecule that inhibits the interaction of a PD-1 axis binding partner with either one or more of its binding partners, so as to remove T cell dysfunction resulting from signaling on the PD-1 signaling axis—with a result being to restore or enhance T cell function (e.g., proliferation, cytokine production, target cell killing). As used herein, a PD-1 axis binding antagonist includes a PD-1 binding antagonist, a PD-L1 binding antagonist, and a PD-L2 binding antagonist.

The term "PD-1 binding antagonist" refers to a molecule that decreases, blocks, inhibits, abrogates or interferes with signal transduction resulting from the interaction of PD-1 with one or more of its binding partners, such as PD-L1, PD-L2. In some embodiments, the PD-1 binding antagonist is a molecule that inhibits the binding of PD-1 to one or more of its binding partners. In a specific embodiment, the PD-1 binding antagonist inhibits the binding of PD-1 to PD-L1 and/or PD-L2. For example, PD-1 binding antagonists include anti-PD-1 antibodies, antigen binding fragments thereof, immunoadhesins, fusion proteins, oligopeptides and other molecules that decrease, block, inhibit, abrogate or interfere with signal transduction resulting from the interaction of PD-1 with PD-L1 and/or PD-L2. In one embodiment, a PD-1 binding antagonist reduces the negative co-stimulatory signal mediated by or through cell surface proteins expressed on T lymphocytes, such as signaling mediated through PD-1, so as render a dysfunctional T cell less dysfunctional (e.g., enhancing effector responses to antigen recognition). In some embodiments, the PD-1 binding antagonist is an anti-PD-1 antibody. In a specific embodiment, a PD-1 binding antagonist is MDX-1106

(nivolumab). In another specific embodiment, a PD-1 binding antagonist is MK-3475 (pembrolizumab). In another specific embodiment, a PD-1 binding antagonist is CT-011 (pidilizumab). In another specific embodiment, a PD-1 binding antagonist is AMP-224. In another specific embodiment, a PD-1 binding antagonist is MED1-0680. In another specific embodiment, a PD-1 binding antagonist is PDR001. In another specific embodiment, a PD-1 binding antagonist is REGN2810. In another specific embodiment, a PD-1 binding antagonist is BGB-108.

The term "PD-L1 binding antagonist" refers to a molecule that decreases, blocks, inhibits, abrogates or interferes with signal transduction resulting from the interaction of PD-L1 with either one or more of its binding partners, such as PD-1, B7-1. In some embodiments, a PD-L1 binding antagonist is a molecule that inhibits the binding of PD-L1 to its binding partners. In a specific embodiment, the PD-L1 binding antagonist inhibits binding of PD-L1 to PD-1 and/or B7-1. In some embodiments, the PD-L1 binding antagonists include anti-PD-L1 antibodies, antigen binding fragments thereof, immunoadhesins, fusion proteins, oligopeptides and other molecules that decrease, block, inhibit, abrogate or interfere with signal transduction resulting from the interaction of PD-L1 with one or more of its binding partners, such as PD-1, B7-1. In one embodiment, a PD-L1 binding antagonist reduces the negative co-stimulatory signal mediated by or through cell surface proteins expressed on T lymphocytes, such as signaling mediated through PD-L1, so as to render a dysfunctional T cell less dysfunctional (e.g., enhancing effector responses to antigen recognition). In some embodiments, a PD-L1 binding antagonist is an anti-PD-L1 antibody. In still another specific embodiment, an anti-PD-L1 antibody is MPDL3280A (atezolizumab). In a specific embodiment, an anti-PD-L1 antibody is YW243.55.S70. In another specific embodiment, an anti-PD-L1 antibody is MDX-1105. In another specific embodiment, an anti PD-L1 antibody is MSB0015718C. In still another specific embodiment, an anti-PD-L1 antibody is MED14736.

The term "PD-L2 binding antagonist" refers to a molecule that decreases, blocks, inhibits, abrogates or interferes with signal transduction resulting from the interaction of PD-L2 with either one or more of its binding partners, such as PD-1. In some embodiments, a PD-L2 binding antagonist is a molecule that inhibits the binding of PD-L2 to one or more of its binding partners. In a specific embodiment, the PD-L2 binding antagonist inhibits binding of PD-L2 to PD-1. In some embodiments, the PD-L2 antagonists include anti-PD-L2 antibodies, antigen binding fragments thereof, immunoadhesins, fusion proteins, oligopeptides and other molecules that decrease, block, inhibit, abrogate or interfere with signal transduction resulting from the interaction of PD-L2 with either one or more of its binding partners, such as PD-1. In one embodiment, a PD-L2 binding antagonist reduces the negative co-stimulatory signal mediated by or through cell surface proteins expressed on T lymphocytes, such as signaling mediated through PD-L2, so as render a dysfunctional T cell less dysfunctional (e.g., enhancing effector responses to antigen recognition). In some embodiments, a PD-L2 binding antagonist is an immunoadhesin.

The term "protein," as used herein, refers to any native protein from any vertebrate source, including mammals such as primates (e.g. humans) and rodents (e.g., mice and rats), unless otherwise indicated. The term encompasses "full-length," unprocessed protein as well as any form of the protein that results from processing in the cell. The term also encompasses naturally occurring variants of the protein, e.g., splice variants or allelic variants. Proteins according to the invention include, for example, any protein listed in Table 1.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

As used herein, "delaying progression" of a disorder or disease means to defer, hinder, slow, retard, stabilize, and/or postpone development of the disease or disorder (e.g., a cell proliferative disorder, e.g., cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

By "reduce" or "inhibit" is meant the ability to cause an overall decrease, for example, of 20% or greater, of 50% or greater, or of 75%, 85%, 90%, 95%, or greater. In certain embodiments, reduce or inhibit can refer to the effector function of an antibody that is mediated by the antibody Fc region, such effector functions specifically including complement-dependent cytotoxicity (CDC), antibody-dependent cellular cytotoxicity (ADCC), and antibody-dependent cellular phagocytosis (ADCP).

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

As used herein, "administering" is meant a method of giving a dosage of a compound (e.g., an anti-HER2 antibody of the invention or a nucleic acid encoding an anti-HER2 antibody of the invention) or a composition (e.g., a pharmaceutical composition, e.g., a pharmaceutical composition including an anti-HER2 antibody of the invention) to a subject. The compositions utilized in the methods described herein can be administered, for example, intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularlly, mucosally, intrapericardially, intraumbilically, intraocularly, orally, topically, locally, by inhalation, by injection, by infusion, by continuous infusion, by localized perfusion bathing target cells directly, by catheter, by lavage, in cremes, or in lipid compositions. The method of administration can vary depending on various factors (e.g., the compound or composition being administered and the severity of the condition, disease, or disorder being treated).

II. Compositions and Methods

The present invention relates to variants of the humanized anti-HER2 antibody hu4D5. In certain embodiments, the anti-HER2 antibodies are bispecific antibodies comprising a HER2 binding domain and a CD3 binding domain. Such bispecific antibodies are referred to as T cell dependent bispecific (TDB) antibodies (also referred to herein as HER2 TDBs).

The anti-HER2 antibodies of the invention are useful, e.g., for the diagnosis or treatment of cancer, including cancers which express HER2 and HER2 positive cancers. In some embodiments, the anti-HER2 antibodies have improved stability as compared to hu4D5. In some instances, the improved stability is related to a decrease in deamidation or isomerization of specific residues present in the HVR regions of hu4D5. Certain anti-HER2 antibodies generated by substitution of amino acids at positions N30, T31, N54, G55, D98, and/or G99 exhibited increased stability associated with reduced deamidation or isomerization. Certain of these anti-HER2 antibodies also surprisingly exhibited increased affinity for the HER2 target.

A. Hu4D5 Variants

In one aspect, the present invention provides an anti-HER2 antibody comprising a light chain variable domain (VL) comprising the amino acid sequence of SEQ ID NO: 1 and a heavy chain variable domain (VH) comprising the amino acid sequence of SEQ ID NO: 2 wherein the light chain variable domain and the heavy chain variable domain comprise amino acid substitutions at one or more positions selected from the group consisting of N30(VL) and T31 (VL), both of SEQ ID NO: 1, and N54(VH), G55(VH), D98(VH) and G99 (VH), all of SEQ ID NO:2, numbered according to the Kabat numbering system.

In one aspect, the present invention provides an anti-HER2 antibody comprising a light chain variable domain comprising the amino acid sequence of SEQ ID NO: 1, wherein the light chain variable domain comprises amino acid substitutions at one or both positions selected from the group consisting of N30(VL) and T31(VL), numbered according to the Kabat numbering system.

In one embodiment, the anti-HER2 antibody comprises a light chain variable domain comprising the amino acid sequence of SEQ ID NO: 1, wherein the light chain variable domain comprises one or more amino acid substitutions selected from the group consisting of N30(VL)S, N30(VL)D, N30(VL)E, N30(VL)T, N30(VL)Q, N30(VL)N, N30(VL)H, N30(VL)K, N30(VL)R, T31(VL)D, T31(VL)V and T31(VL)S.

In one embodiment, the anti-HER2 antibody comprises a light chain variable domain comprising the amino acid sequence of SEQ ID NO: 1, wherein the light chain variable domain comprises an amino acid substitution at N30(VL). In one embodiment, the anti-HER2 antibody comprises a light chain variable domain comprising the amino acid sequence of SEQ ID NO: 1, wherein the light chain variable domain comprises the amino acid substitution N30(VL)S. In one embodiment, the anti-HER2 antibody comprises a light chain variable domain comprising the amino acid sequence of SEQ ID NO: 1, wherein the light chain variable domain comprises the amino acid substitution N30(VL)D. In one embodiment, the anti-HER2 antibody comprises a light chain variable domain comprising the amino acid sequence of SEQ ID NO: 1, wherein the light chain variable domain comprises the amino acid substitution N30(VL)E. In one embodiment, the anti-HER2 antibody comprises a light chain variable domain comprising the amino acid sequence of SEQ ID NO: 1, wherein the light chain variable domain comprises the amino acid substitution N30(VL)T. In one embodiment, the anti-HER2 antibody comprises a light chain variable domain comprising the amino acid sequence of SEQ ID NO: 1, wherein the light chain variable domain comprises the amino acid substitution N30(VL)Q.

In one embodiment, the anti-HER2 antibody comprises a light chain variable domain comprising the amino acid sequence of SEQ ID NO: 1, wherein the light chain variable domain comprises an amino acid substitution at N31(VL). In one embodiment, the anti-HER2 antibody comprises a light chain variable domain comprising the amino acid sequence of SEQ ID NO: 1, wherein the light chain variable domain comprises the amino acid substitution T31(VL)D.

In one aspect, the present invention provides an anti-HER2 antibody comprising a heavy chain variable domain comprising the amino acid sequence of SEQ ID NO: 2, wherein the heavy chain variable domain comprises amino acid substitutions at one or both of positions selected from the group consisting of N54(VH) and G55(VH), numbered according to the Kabat numbering system.

In one embodiment, the anti-HER2 antibody comprises a heavy chain variable domain comprising the amino acid sequence of SEQ ID NO: 2, wherein the heavy chain variable domain comprises one or more amino acid substitution selected from the group consisting of N54(VH)E, N54(VH)A, N54(VH)S, N54(VH)Q, N54(VH)H, N54(VH)D, N54(VH)K, N54(VH)R, and G55(VH)A.

In one embodiment, the anti-HER2 antibody comprises a heavy chain variable domain comprising the amino acid sequence of SEQ ID NO: 2, wherein the heavy chain variable domain comprises an amino acid substitution at N54(VH). In one embodiment, the anti-HER2 antibody comprises a heavy chain variable domain comprising the amino acid sequence of SEQ ID NO: 2, wherein the heavy chain variable domain comprises the amino acid substitution N54(VH)E. In one embodiment, the anti-HER2 antibody comprises a heavy chain variable domain comprising the amino acid sequence of SEQ ID NO: 2, wherein the heavy chain variable domain comprises the amino acid substitution N54(VH)A. In one embodiment, the anti-HER2 antibody comprises a heavy chain variable domain comprising the amino acid sequence of SEQ ID NO: 2, wherein the heavy chain variable domain comprises the amino acid substitution N54(VH)S.

In one embodiment, the anti-HER2 antibody comprises a heavy chain variable domain comprising the amino acid sequence of SEQ ID NO: 2, wherein the heavy chain variable domain comprises an amino acid substitution at G55(VH). In one embodiment, the anti-HER2 antibody comprises a heavy chain variable domain comprising the amino acid sequence of SEQ ID NO: 2, wherein the heavy chain variable domain comprises the amino acid substitution G55(VH)A.

In one aspect, the present invention relates to an anti-HER2 antibody comprising a heavy chain variable domain comprising the amino acid sequence of SEQ ID NO: 2, wherein the heavy chain variable domain comprises amino acid substitutions at one or both of positions selected from the group consisting of D98(VH) and G99(VH), numbered according to the Kabat numbering system.

In one embodiment, the anti-HER2 antibody comprises a heavy chain variable domain comprising the amino acid sequence of SEQ ID NO: 2, wherein the heavy chain variable domain comprises an amino acid substitution selected from the group consisting of D98(VH)T, D98VH)E, D98(VH)N, D98(VH)S, G99(VH)S, G99(VH)A and G99(VH)T.

In one embodiment, the anti-HER2 antibody comprises a heavy chain variable domain comprising the amino acid sequence of SEQ ID NO: 2, wherein the heavy chain variable domain comprises an amino acid substitution at D98(VH). In one embodiment, the anti-HER2 antibody comprises a heavy chain variable domain comprising the amino acid sequence of SEQ ID NO: 2, wherein the heavy chain variable domain comprises the amino acid substitution D98(VH)T. In one embodiment, the anti-HER2 antibody comprises a heavy chain variable domain comprising the amino acid sequence of SEQ ID NO: 2, wherein the heavy chain variable domain comprises the amino acid substitution D98(VH)E. In one embodiment, the anti-HER2 antibody comprises a heavy chain variable domain comprising the amino acid sequence of SEQ ID NO: 2, wherein the heavy chain variable domain comprises the amino acid substitution D98(VH)S.

In one embodiment, the anti-HER2 antibody comprises a heavy chain variable domain comprising the amino acid sequence of SEQ ID NO: 2, wherein the heavy chain variable domain comprises an amino acid substitution at G99(VH). In one embodiment, the anti-HER2 antibody comprises a heavy chain variable domain comprising the amino acid sequence of SEQ ID NO: 2, wherein the heavy chain variable domain comprises the amino acid substitution G99(VH)S. In one embodiment, anti-HER2 antibody comprises a heavy chain variable domain comprising the amino acid sequence of SEQ ID NO: 2, wherein the heavy chain variable domain comprises the amino acid substitution G99(VH)T.

In one aspect, the present invention relates to an anti-HER2 antibody comprising a light chain variable domain (VL) comprising the amino acid sequence of SEQ ID NO: 3 and a heavy chain variable domain (VH) comprising the amino acid sequence of SEQ ID NO: 4.

(SEQ ID NO: 3)
DIQMTQSPSSLSASVGDRVTITCRASQDVX$_1$X$_2$AVAWYQQKPGKAPKLL

IYSASFLYSGVPSRFSGSRSGTDFTLTISSLQPEDFATYYCQQHYTTP

PTFGQGTKVEIK

Where $X_1$ is N, D, S, T, E, H, K, R, or Q and $X_2$ is T, V, S or D.

(SEQ ID NO: 4)
EVQLVESGGGLVQPGGSLRLSCAASGFNIKDTYIHWVRQAPGKGLEWVAR

IYPTX$_3$X$_4$YTRYADSVKGRFTISADTSKNTAYLQMNSLRAEDTAVYYCSRW

GGX$_5$X$_6$FYAMDYWGQGTLVTVSS

Where $X_3$ is N, E, A, Q, H, D, K, R, or S; $X_4$ is G or A; $X_5$ is D, E, S, N or T, and $X_6$ is G, S, A or T.

In one aspect, the present invention relates to an anti-HER2 antibody comprising a light chain variable domain (VL) and comprising a heavy chain variable domain (VH) comprising the amino acid sequence of SEQ ID NO: 5.

```
                                             (SEQ ID NO: 5)
EVQLVESGGGLVQPGGSLRLSCAASGFNIKDTYIHWVRQAPGKGLEWVAR

IYPTNX₇YTRYADSVKGRFTISADTSKNTAYLQMNSLRAEDTAVYYCSRW

GGDGFYAMDYWGQGTLVTVSS
```

Where $X_7$ is an amino acid other than G. In one embodiment, $X_7$ is A.

In one aspect, the present invention relates to an anti-HER2 antibody comprising a light chain variable domain (VL) comprising the amino acid sequence of SEQ ID NO: 3 and a heavy chain variable domain (VH) comprising the amino acid sequence of SEQ ID NO: 5.

In one aspect, the present invention relates to an anti-HER2 antibody comprising a light chain variable domain (VL) comprising the amino acid sequence of SEQ ID NO: 1 and a heavy chain variable domain (VH) comprising the amino acid sequence of SEQ ID NO: 5.

In one aspect, the present invention provides an anti-HER2 antibody comprising a HER2 binding domain comprising at least one, two, three, four, five, or six HVRs selected from: (a) an HVR-H1 comprising the amino acid sequence of SEQ ID NO:50; (b) an HVR-H2 comprising the amino acid sequence of SEQ ID NO:57; (c) an HVR-H3 comprising the amino acid sequence of SEQ ID NO:62; (d) an HVR-L1 comprising the amino acid sequence of SEQ ID NO: 53; (e) an HVR-L2 comprising the amino acid sequence of SEQ ID NO:48; and (f) an HVR-L3 comprising the amino acid sequence of SEQ ID NO:49.

In one aspect, the invention provides an anti-HER2 antibody comprising a HER2 binding domain comprising at least one, at least two, or all three VH HVR sequences selected from (a) an HVR-H1 comprising the amino acid sequence of SEQ ID NO:50; (b) an HVR-H2 comprising the amino acid sequence of SEQ ID NO:57; (c) an HVR-H3 comprising the amino acid sequence of SEQ ID NO:62. In a further embodiment, the HER2 binding domain comprises (a) an HVR-H1 comprising the amino acid sequence of SEQ ID NO:50; (b) an HVR-H2 comprising the amino acid sequence of SEQ ID NO:57; (c) an HVR-H3 comprising the amino acid sequence of SEQ ID NO:62.

In another aspect, the invention provides an anti-HER2 antibody comprising a HER2 binding domain comprising at least one, at least two, or all three VL HVR sequences selected from (a) an HVR-L1 comprising the amino acid sequence of SEQ ID NO: 53; (b) an HVR-L2 comprising the amino acid sequence of SEQ ID NO:48; and (c) an HVR-L3 comprising the amino acid sequence of SEQ ID NO:49. In a further embodiment, the HER2 binding domain comprise (a) an HVR-L1 comprising the amino acid sequence of SEQ ID NO: 53; (b) an HVR-L2 comprising the amino acid sequence of SEQ ID NO:48; and (c) an HVR-L3 comprising the amino acid sequence of SEQ ID NO:49.

In one aspect, the present invention provides an anti-HER2 antibody comprising a HER2 binding domain comprising (a) an HVR-H1 comprising the amino acid sequence of SEQ ID NO:50; (b) an HVR-H2 comprising the amino acid sequence of SEQ ID NO:57; (c) an HVR-H3 comprising the amino acid sequence of SEQ ID NO:62; (d) an HVR-L1 comprising the amino acid sequence of SEQ ID NO: 53; (e) an HVR-L2 comprising the amino acid sequence of SEQ ID NO:48; and (f) an HVR-L3 comprising the amino acid sequence of SEQ ID NO:49.

In one aspect, the present invention provides an anti-HER2 antibody comprising a HER2 binding domain comprising at least one, two, three, four, five, or six HVRs selected from: (a) an HVR-H1 comprising the amino acid sequence of SEQ ID NO:50; (b) an HVR-H2 comprising the amino acid sequence of SEQ ID NO:57; (c) an HVR-H3 comprising the amino acid sequence of SEQ ID NO:63; (d) an HVR-L1 comprising the amino acid sequence of SEQ ID NO: 54; (e) an HVR-L2 comprising the amino acid sequence of SEQ ID NO:48; and (f) an HVR-L3 comprising the amino acid sequence of SEQ ID NO:49.

In one aspect, the invention provides an anti-HER2 antibody comprising a HER2 binding domain comprising at least one, at least two, or all three VH HVR sequences selected from: (a) an HVR-H1 comprising the amino acid sequence of SEQ ID NO:50; (b) an HVR-H2 comprising the amino acid sequence of SEQ ID NO:57; (c) an HVR-H3 comprising the amino acid sequence of SEQ ID NO:63. In a further embodiment, the HER2 binding domain comprises: (a) an HVR-H1 comprising the amino acid sequence of SEQ ID NO:50; (b) an HVR-H2 comprising the amino acid sequence of SEQ ID NO:57; (c) an HVR-H3 comprising the amino acid sequence of SEQ ID NO:63.

In another aspect, the invention provides an anti-HER2 antibody comprising a HER2 binding domain comprising at least one, at least two, or all three VL HVR sequences selected from (a) an HVR-L1 comprising the amino acid sequence of SEQ ID NO: 54; (b) an HVR-L2 comprising the amino acid sequence of SEQ ID NO:48; and (c) an HVR-L3 comprising the amino acid sequence of SEQ ID NO:49. In a further embodiment, the HER2 binding domain comprise (a) an HVR-L1 comprising the amino acid sequence of SEQ ID NO: 54; (b) an HVR-L2 comprising the amino acid sequence of SEQ ID NO:48; and (c) an HVR-L3 comprising the amino acid sequence of SEQ ID NO:49.

In one aspect, the present invention provides an anti-HER2 antibody comprising a HER2 binding domain: (a) an HVR-H1 comprising the amino acid sequence of SEQ ID NO:50; (b) an HVR-H2 comprising the amino acid sequence of SEQ ID NO:57; (c) an HVR-H3 comprising the amino acid sequence of SEQ ID NO:63; (d) an HVR-L1 comprising the amino acid sequence of SEQ ID NO: 54; (e) an HVR-L2 comprising the amino acid sequence of SEQ ID NO:48; and (f) an HVR-L3 comprising the amino acid sequence of SEQ ID NO:49.

In one aspect, the present invention provides an anti-HER2 antibody comprising a HER2 binding domain comprising at least one, two, three, four, five, or six HVRs selected from: (a) an HVR-H1 comprising the amino acid sequence of SEQ ID NO:50; (b) an HVR-H2 comprising the amino acid sequence of SEQ ID NO:58; (c) an HVR-H3 comprising the amino acid sequence of SEQ ID NO:63; (d) an HVR-L1 comprising the amino acid sequence of SEQ ID NO: 54; (e) an HVR-L2 comprising the amino acid sequence of SEQ ID NO:48; and (f) an HVR-L3 comprising the amino acid sequence of SEQ ID NO:49.

In one aspect, the invention provides an anti-HER2 antibody comprising a HER2 binding domain comprising at least one, at least two, or all three VH HVR sequences selected from (a) an HVR-H1 comprising the amino acid sequence of SEQ ID NO:50; (b) an HVR-H2 comprising the amino acid sequence of SEQ ID NO:58; (c) an HVR-H3 comprising the amino acid sequence of SEQ ID NO:63. In a further embodiment, the HER2 binding domain comprises an HVR-H2 comprising the amino acid sequence of SEQ ID NO:58. In a further embodiment, the HER2 binding domain comprises (a) an HVR-H1 comprising the amino acid sequence of SEQ ID NO:50; (b) an HVR-H2 comprising the amino acid sequence of SEQ ID NO:58; (c) an HVR-H3 comprising the amino acid sequence of SEQ ID NO:63.

In one aspect, the present invention provides an anti-HER2 antibody comprising a HER2 binding domain comprising (a) an HVR-H1 comprising the amino acid sequence of SEQ ID NO:50; (b) an HVR-H2 comprising the amino acid sequence of SEQ ID NO:58; (c) an HVR-H3 comprising the amino acid sequence of SEQ ID NO:63; (d) an HVR-L1 comprising the amino acid sequence of SEQ ID NO: 54; (e) an HVR-L2 comprising the amino acid sequence of SEQ ID NO:48; and (f) an HVR-L3 comprising the amino acid sequence of SEQ ID NO:49.

In one aspect, the present invention provides an anti-HER2 antibody comprising a HER2 binding domain comprising at least one, two, three, four, five, or six HVRs selected from: (a) an HVR-H1 comprising the amino acid sequence of SEQ ID NO:50; (b) an HVR-H2 comprising the amino acid sequence of SEQ ID NO:51; (c) an HVR-H3 comprising the amino acid sequence of SEQ ID NO:62; (d) an HVR-L1 comprising the amino acid sequence of SEQ ID NO: 54; (e) an HVR-L2 comprising the amino acid sequence of SEQ ID NO:48; and (f) an HVR-L3 comprising the amino acid sequence of SEQ ID NO:49.

In one aspect, the invention provides an anti-HER2 antibody comprising a HER2 binding domain comprising at least one, at least two, or all three VH HVR sequences selected from (a) an HVR-H1 comprising the amino acid sequence of SEQ ID NO:50; (b) an HVR-H2 comprising the amino acid sequence of SEQ ID NO:51; (c) an HVR-H3 comprising the amino acid sequence of SEQ ID NO:62. In a further embodiment, the HER2 binding domain comprises: (a) an HVR-H1 comprising the amino acid sequence of SEQ ID NO:50; (b) an HVR-H2 comprising the amino acid sequence of SEQ ID NO:51; (c) an HVR-H3 comprising the amino acid sequence of SEQ ID NO:62.

In one aspect, the present invention provides an anti-HER2 antibody comprising a HER2 binding domain comprising: (a) an HVR-H1 comprising the amino acid sequence of SEQ ID NO:50; (b) an HVR-H2 comprising the amino acid sequence of SEQ ID NO:51; (c) an HVR-H3 comprising the amino acid sequence of SEQ ID NO:62; (d) an HVR-L1 comprising the amino acid sequence of SEQ ID NO: 54; (e) an HVR-L2 comprising the amino acid sequence of SEQ ID NO:48; and (f) an HVR-L3 comprising the amino acid sequence of SEQ ID NO:49.

In one aspect, the present invention provides an anti-HER2 antibody comprising a HER2 binding domain comprising at least one, two, three, four, five, or six HVRs selected from: (a) an HVR-H1 comprising the amino acid sequence of SEQ ID NO:50; (b) an HVR-H2 comprising the amino acid sequence of SEQ ID NO:58; (c) an HVR-H3 comprising the amino acid sequence of SEQ ID NO:63; (d) an HVR-L1 comprising the amino acid sequence of SEQ ID NO: 55; (e) an HVR-L2 comprising the amino acid sequence of SEQ ID NO:48; and (f) an HVR-L3 comprising the amino acid sequence of SEQ ID NO:49.

In one aspect, the invention provides an anti-HER2 antibody comprising a HER2 binding domain comprising at least one, at least two, or all three VH HVR sequences selected from: (a) an HVR-H1 comprising the amino acid sequence of SEQ ID NO:50; (b) an HVR-H2 comprising the amino acid sequence of SEQ ID NO:58; (c) an HVR-H3 comprising the amino acid sequence of SEQ ID NO:63. In a further embodiment, the HER2 binding domain comprises: (a) an HVR-H1 comprising the amino acid sequence of SEQ ID NO:50; (b) an HVR-H2 comprising the amino acid sequence of SEQ ID NO:58; (c) an HVR-H3 comprising the amino acid sequence of SEQ ID NO:63.

In another aspect, the invention provides an anti-HER2 antibody comprising a HER2 binding domain comprising at least one, at least two, or all three VL HVR sequences selected from (a) an HVR-L1 comprising the amino acid sequence of SEQ ID NO: 55; (b) an HVR-L2 comprising the amino acid sequence of SEQ ID NO:48; and (c) an HVR-L3 comprising the amino acid sequence of SEQ ID NO:49. In a further embodiment, the HER2 binding domain comprises (a) an HVR-L1 comprising the amino acid sequence of SEQ ID NO: 55; (b) an HVR-L2 comprising the amino acid sequence of SEQ ID NO:48; and (c) an HVR-L3 comprising the amino acid sequence of SEQ ID NO:49.

In one aspect, the present invention provides an anti-HER2 antibody comprising a HER2 binding domain comprising (a) an HVR-H1 comprising the amino acid sequence of SEQ ID NO:50; (b) an HVR-H2 comprising the amino acid sequence of SEQ ID NO:58; (c) an HVR-H3 comprising the amino acid sequence of SEQ ID NO:63; (d) an HVR-L1 comprising the amino acid sequence of SEQ ID NO: 55; (e) an HVR-L2 comprising the amino acid sequence of SEQ ID NO:48; and (f) an HVR-L3 comprising the amino acid sequence of SEQ ID NO:49.

In one aspect, the present invention provides an anti-HER2 antibody comprising a HER2 binding domain comprising at least one, two, three, four, five, or six HVRs selected from: (a) an HVR-H1 comprising the amino acid sequence of SEQ ID NO:50; (b) an HVR-H2 comprising the amino acid sequence of SEQ ID NO:51; (c) an HVR-H3 comprising the amino acid sequence of SEQ ID NO:63; (d) an HVR-L1 comprising the amino acid sequence of SEQ ID NO: 54; (e) an HVR-L2 comprising the amino acid sequence of SEQ ID NO:48; and (f) an HVR-L3 comprising the amino acid sequence of SEQ ID NO:49.

In one aspect, the invention provides an anti-HER2 antibody comprising a HER2 binding domain comprising at least one, at least two, or all three VH HVR sequences selected from: (a) an HVR-H1 comprising the amino acid sequence of SEQ ID NO:50; (b) an HVR-H2 comprising the amino acid sequence of SEQ ID NO:51; (c) an HVR-H3 comprising the amino acid sequence of SEQ ID NO:63. In a further embodiment, the HER2 binding domain comprises: (a) an HVR-H1 comprising the amino acid sequence of SEQ ID NO:50; (b) an HVR-H2 comprising the amino acid sequence of SEQ ID NO:51; (c) an HVR-H3 comprising the amino acid sequence of SEQ ID NO:63.

In one aspect, the present invention provides an anti-HER2 antibody comprising a HER2 binding domain comprising: (a) an HVR-H1 comprising the amino acid sequence of SEQ ID NO:50; (b) an HVR-H2 comprising the amino acid sequence of SEQ ID NO:51; (c) an HVR-H3 comprising the amino acid sequence of SEQ ID NO:63; (d) an HVR-L1 comprising the amino acid sequence of SEQ ID NO: 54; (e) an HVR-L2 comprising the amino acid sequence of SEQ ID NO:48; and (f) an HVR-L3 comprising the amino acid sequence of SEQ ID NO:49.

In one aspect, the present invention provides an anti-HER2 antibody comprising a HER2 binding domain comprising at least one, two, three, four, five, or six HVRs selected from: (a) an HVR-H1 comprising the amino acid sequence of SEQ ID NO:50; (b) an HVR-H2 comprising the amino acid sequence of SEQ ID NO:51; (c) an HVR-H3 comprising the amino acid sequence of SEQ ID NO:65; (d) an HVR-L1 comprising the amino acid sequence of SEQ ID NO: 54; (e) an HVR-L2 comprising the amino acid sequence of SEQ ID NO:48; and (f) an HVR-L3 comprising the amino acid sequence of SEQ ID NO:49.

In one aspect, the invention provides an anti-HER2 antibody comprising a HER2 binding domain comprising at least one, at least two, or all three VH HVR sequences selected from: (a) an HVR-H1 comprising the amino acid sequence of SEQ ID NO:50; (b) an HVR-H2 comprising the amino acid sequence of SEQ ID NO:51; (c) an HVR-H3 comprising the amino acid sequence of SEQ ID NO:65. In a further embodiment, the HER2 binding domain comprises (a) an HVR-H1 comprising the amino acid sequence of SEQ ID NO:50; (b) an HVR-H2 comprising the amino acid sequence of SEQ ID NO:51; (c) an HVR-H3 comprising the amino acid sequence of SEQ ID NO:65.

In one aspect, the present invention provides an anti-HER2 antibody comprising a HER2 binding domain comprising: (a) an HVR-H1 comprising the amino acid sequence of SEQ ID NO:50; (b) an HVR-H2 comprising the amino acid sequence of SEQ ID NO:51; (c) an HVR-H3 comprising the amino acid sequence of SEQ ID NO:65; (d) an HVR-L1 comprising the amino acid sequence of SEQ ID NO:54; (e) an HVR-L2 comprising the amino acid sequence of SEQ ID NO:48; and (f) an HVR-L3 comprising the amino acid sequence of SEQ ID NO:49.

In one aspect, the present invention provides an anti-HER2 antibody comprising a HER2 binding domain comprising at least one, two, three, four, five, or six HVRs selected from: (a) an HVR-H1 comprising the amino acid sequence of SEQ ID NO:50; (b) an HVR-H2 comprising the amino acid sequence of SEQ ID NO:58; (c) an HVR-H3 comprising the amino acid sequence of SEQ ID NO:63; (d) an HVR-L1 comprising the amino acid sequence of SEQ ID NO: 53; (e) an HVR-L2 comprising the amino acid sequence of SEQ ID NO:48; and (f) an HVR-L3 comprising the amino acid sequence of SEQ ID NO:49.

In one aspect, the invention provides an anti-HER2 antibody comprising a HER2 binding domain comprising at least one, at least two, or all three VH HVR sequences selected from: (a) an HVR-H1 comprising the amino acid sequence of SEQ ID NO:50; (b) an HVR-H2 comprising the amino acid sequence of SEQ ID NO:58; (c) an HVR-H3 comprising the amino acid sequence of SEQ ID NO:63. In a further embodiment, the HER2 binding domain comprises (a) an HVR-H1 comprising the amino acid sequence of SEQ ID NO:50; (b) an HVR-H2 comprising the amino acid sequence of SEQ ID NO:58; (c) an HVR-H3 comprising the amino acid sequence of SEQ ID NO:63.

In one aspect, the present invention provides an anti-HER2 antibody comprising a HER2 binding domain comprising: (a) an HVR-H1 comprising the amino acid sequence of SEQ ID NO:50; (b) an HVR-H2 comprising the amino acid sequence of SEQ ID NO:58; (c) an HVR-H3 comprising the amino acid sequence of SEQ ID NO:63; (d) an HVR-L1 comprising the amino acid sequence of SEQ ID NO:53; (e) an HVR-L2 comprising the amino acid sequence of SEQ ID NO:48; and (f) an HVR-L3 comprising the amino acid sequence of SEQ ID NO:49.

In one aspect, the present invention provides an anti-HER2 antibody comprising a HER2 binding domain comprising at least one, two, three, four, five, or six HVRs selected from: (a) an HVR-H1 comprising the amino acid sequence of SEQ ID NO:50; (b) an HVR-H2 comprising the amino acid sequence of SEQ ID NO:51; (c) an HVR-H3 comprising the amino acid sequence of SEQ ID NO:63; (d) an HVR-L1 comprising the amino acid sequence of SEQ ID NO: 55; (e) an HVR-L2 comprising the amino acid sequence of SEQ ID NO:48; and (f) an HVR-L3 comprising the amino acid sequence of SEQ ID NO:49.

In one aspect, the invention provides an anti-HER2 antibody comprising a HER2 binding domain comprising at least one, at least two, or all three VH HVR sequences selected from: (a) an HVR-H1 comprising the amino acid sequence of SEQ ID NO:50; (b) an HVR-H2 comprising the amino acid sequence of SEQ ID NO:51; (c) an HVR-H3 comprising the amino acid sequence of SEQ ID NO:63. In a further embodiment, the HER2 binding domain comprises (a) an HVR-H1 comprising the amino acid sequence of SEQ ID NO:50; (b) an HVR-H2 comprising the amino acid sequence of SEQ ID NO:51; (c) an HVR-H3 comprising the amino acid sequence of SEQ ID NO:63.

In one aspect, the present invention provides an anti-HER2 antibody comprising a HER2 binding domain comprising: (a) an HVR-H1 comprising the amino acid sequence of SEQ ID NO:50; (b) an HVR-H2 comprising the amino acid sequence of SEQ ID NO:51; (c) an HVR-H3 comprising the amino acid sequence of SEQ ID NO:63; (d) an HVR-L1 comprising the amino acid sequence of SEQ ID NO:55; (e) an HVR-L2 comprising the amino acid sequence of SEQ ID NO:48; and (f) an HVR-L3 comprising the amino acid sequence of SEQ ID NO:49.

In any of the above embodiments, an anti-HER2 antibody comprising a HER2 binding domain is humanized. In one embodiment, an anti-HER2 antibody comprising a HER2 binding domain comprises HVRs as in any of the above embodiments, and further comprises a human acceptor framework, e.g. a human immunoglobulin framework or a human consensus framework. In certain embodiments, the human acceptor framework is the human VL kappa I consensus ($VL_{KI}$) framework and/or the VH framework $VH_1$.

In one aspect, the present invention relates to an anti-HER2 antibody comprising a light chain variable domain (VL) comprising the amino acid sequence of SEQ ID NO: 6 and a heavy chain variable domain (VH) comprising the amino acid sequence of SEQ ID NO: 7.

In one aspect, the present invention relates to an anti-HER2 antibody comprising a light chain variable domain (VL) comprising the amino acid sequence of SEQ ID NO: 8 and a heavy chain variable domain (VH) comprising the amino acid sequence of SEQ ID NO: 9.

In one aspect, the present invention relates to an anti-HER2 antibody comprising a light chain variable domain (VL) comprising the amino acid sequence of SEQ ID NO: 10 and a heavy chain variable domain (VH) comprising the amino acid sequence of SEQ ID NO: 11.

In one aspect, the present invention relates to an anti-HER2 antibody comprising a light chain variable domain (VL) comprising the amino acid sequence of SEQ ID NO: 12 and a heavy chain variable domain (VH) comprising the amino acid sequence of SEQ ID NO: 13.

In one aspect, the present invention relates to an anti-HER2 antibody comprising a light chain variable domain (VL) comprising the amino acid sequence of SEQ ID NO: 14 and a heavy chain variable domain (VH) comprising the amino acid sequence of SEQ ID NO: 15.

In one aspect, the present invention relates to an anti-HER2 antibody comprising a light chain variable domain (VL) comprising the amino acid sequence of SEQ ID NO:16 and a heavy chain variable domain (VH) comprising the amino acid sequence of SEQ ID NO: 17.

In one aspect, the present invention relates to an anti-HER2 antibody comprising a light chain variable domain (VL) comprising the amino acid sequence of SEQ ID NO:

18 and a heavy chain variable domain (VH) comprising the amino acid sequence of SEQ ID NO: 19.

In one aspect, the present invention relates to an anti-HER2 antibody comprising a light chain variable domain (VL) comprising the amino acid sequence of SEQ ID NO: 20 and a heavy chain variable domain (VH) comprising the amino acid sequence of SEQ ID NO: 21.

In one aspect, the present invention relates to an anti-HER2 antibody comprising a light chain variable domain (VL) comprising the amino acid sequence of SEQ ID NO: 22 and a heavy chain variable domain (VH) comprising the amino acid sequence of SEQ ID NO: 23.

In another aspect, an anti-HER2 antibody comprising a HER2 binding domain is provided, wherein the antibody comprises a VH as in any of the embodiments provided above, and a VL as in any of the embodiments provided above, including post-translational modifications of those sequences.

In a further aspect of the invention, an anti-HER2 antibody comprising a HER2 binding domain according to any of the above embodiments is a monoclonal antibody, including a human antibody. In one embodiment, an anti-HER2 antibody comprising a HER2 binding domain is an antibody fragment, e.g., a Fv, Fab, Fab', scFv, diabody, or F(ab')2 fragment. In another embodiment, the antibody is a substantially full length antibody, e.g., an IgG1 antibody, IgG2a antibody or other antibody class or isotype as defined herein.

Figure 1:
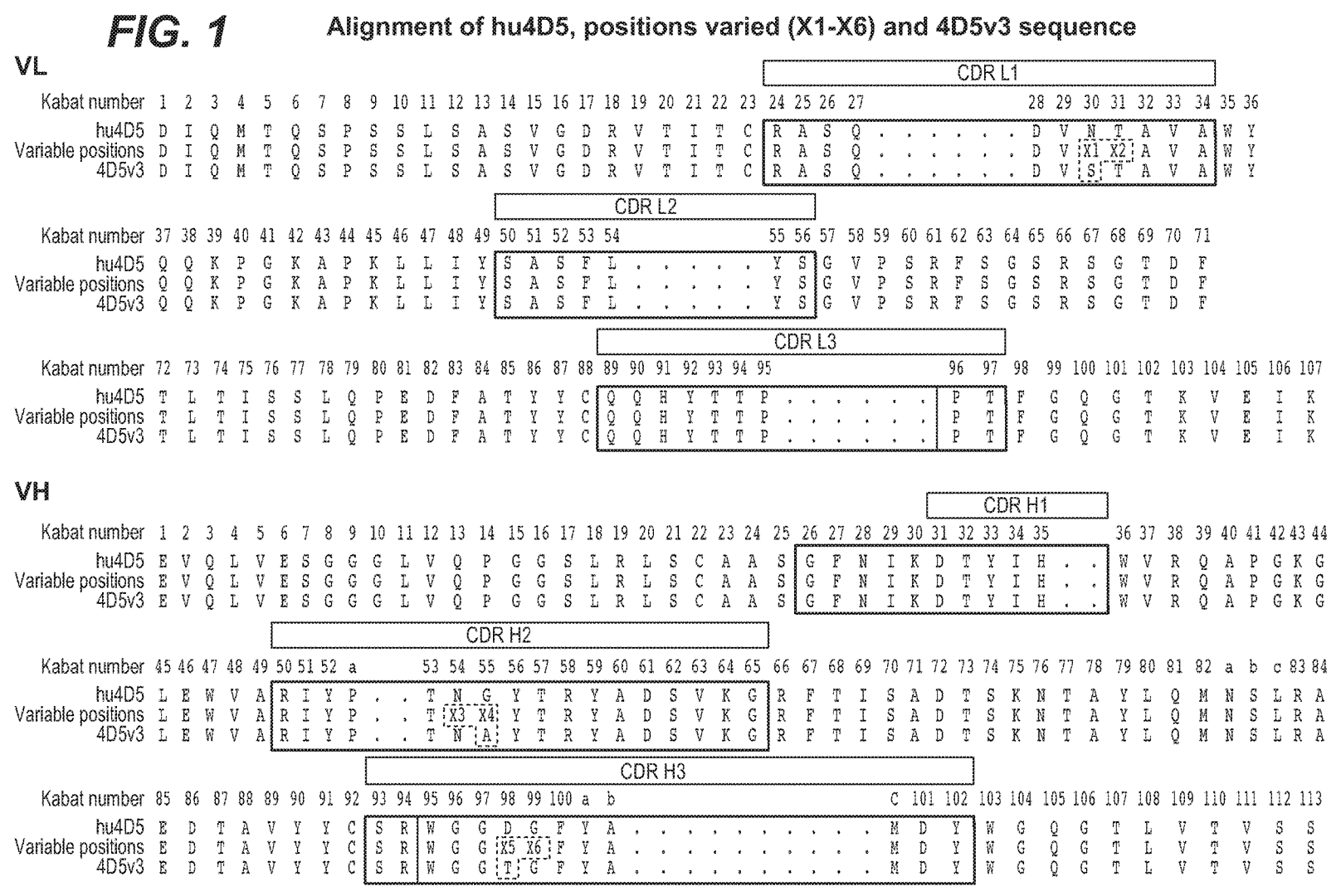

Provided herein are anti-HER2 antibodies comprising a HER2 binding domain comprising a light chain variable domain comprising HVRs with the amino acid substitutions as compared to hu4D5 as shown in FIGS. 1, 3, and 4.

HER2 TDBs

In any one of the above aspects, the anti-Her2 antibody provided herein is is a T cell dependent bispecific (TDB) antibody, wherein one of the binding specificities is for HER2 and the other is for CD3 (e.g., CD3ε or CD3γ).

In some embodiments, the CD3 binding domain of the anti-HER2 antibody binds to a human CD3 polypeptide or a cynomolgus monkey (cyno) CD3 polypeptide. In some embodiments, the human CD3 polypeptide or the cyno CD3 polypeptide is a human CD3ε polypeptide or a cyno CD3ε polypeptide, respectively. In some embodiments, the human CD3 polypeptide or the cyno CD3 polypeptide is a human CD3γ polypeptide or a cyno CD3γ polypeptide, respectively. In certain embodiments, an anti-HER2 antibody is provided comprising a CD3 binding domain which binds to an epitope within a fragment of CD3 (e.g., human CD3ε) consisting of amino acids 1-26 or 1-27 of human CD3ε. In some embodiments, the anti-HER2 antibody is a bispecific antibody. In some embodiments, the anti-HER2 antibody is a bispecific IgG antibody.

In some embodiments, CD3 binding domain binds the human CD3ε polypeptide with a Kd of 250 nM or lower. In some embodiments, the CD3 binding domain binds the human CD3ε polypeptide with a Kd of 100 nM or lower. In some embodiments, the CD3 binding domain binds the human CD3ε polypeptide with a Kd of 15 nM or lower. In some embodiments, CD3 binding domain binds the human CD3ε polypeptide with a Kd of 10 nM or lower. In some embodiments, CD3 binding domain binds the human CD3ε polypeptide with a Kd of 5 nM or lower. In some embodiments, the CD3 binding arm of the anti-HER2 antibody binds human CD3 with an affinity less than 50 nM and greater than 1 nM. In some embodiments, the CD3 binding arm of the anti-HER2 antibody binds human CD3 with an affinity less than 1 nM and greater than 0.1 nM. In some embodiments, the CD3 binding arm of the anti-HER2 antibody binds human CD3 with an affinity less than 0.1 nM and greater than 0.01 nM. In some embodiments, the affinity of the CD3 binding arm is determined by Biacore. In some embodiments, the human CD3 is hCD3εγ. In some embodiments, the human CD3 is hCD3ε 1-27 Fc.

In some embodiments, the CD3 binding domain of the anti-HER2 antibody binds contacts with amino acids of human CD3ε at a distance of 3.5 Angstroms, 3.25 Angstroms, 3.00 Angstroms, 2.75 Angstroms, or less. In certain embodiments, the CD3 binding domain is provided that binds to an epitope consisting of one, two, three, four, or five amino acids of human CD3ε at a distance of 3.5 Angstroms, 3.25 Angstroms, 3.00 Angstroms, 2.75 Angstroms or less. In one embodiment, the CD3 binding domain of the anti-HER2 antibody makes unique contacts with amino acids of human CD3ε at a distance of 3.5 Angstroms or less. In certain embodiments, the CD3 binding domain is provided that binds to an epitope consisting of one, two, three, four, or five amino acids of human CD3ε at a distance of 3.5 Angstroms or less. For example, in certain embodiments, the CD3 binding domain is provided that binds to an epitope consisting of amino acids of human CD3ε selected from Gln1, Asp2, Asn4, Glu6, and Met7. In one particular embodiment, the CD3 binding domain binds to an epitope that specifically includes Glu6. In certain other embodiments, the CD3 binding domain is provided that does not bind to an epitope that includes human CD3ε amino acid Glu5. In certain other embodiments, the CD3 binding domain is provided that does not bind to an epitope that includes human CD3ε amino acids Gly3 and Glu5.

A CD3 epitope may be determined by the CD3 binding domain binding to peptide fragments of the epitope. Alternatively, a CD3 epitope may be determined by alanine scanning mutagenesis. In one embodiment, a reduction in binding of a CD3 binding domain to mutated CD3 by 20%, 30%, 50%, 80% or more indicates the amino acid residue of CD3 mutated in an alanine scanning mutagenesis assay is an epitope residue for that CD3 binding domain. Alternatively, a CD3 epitope may be determined by mass spectrometry. In some embodiments, the epitope is determined by crystallography (e.g., crystallography methods).

In some embodiments, the CD3 epitope as determined by crystallography is determined using amino acids Q1-M7 of CD3. In some embodiments, the CD3 epitope as determined by crystallography is determined using amino acids QDGNEEMGGITQTPYK (SEQ ID NO: 89) of CD3.

In some embodiments, the CD3 epitope as determined by crystallography may be performed by combining the anti-CD3 antibody Fab, dissolved in 0.15 M NaCl, 25 mM tris, pH 7.5 at 10 mg/ml, with a 2-fold molar excess (1 mg) of CD3ε peptide and initially screening a sparse matrix of precipitants in a sitting drop vapor diffusion format. Optimized crystals may be grown from a 1:1 mixture with reservoir solution containing 70% v/v methyl-pentanediol, and 0.1 M HEPES buffer at pH 7.5. The reservoir may be be used as a cryoprotectant. The crystals may be transferred to cryogenic temperature by sudden immersion into liquid nitrogen.

The diffraction data for crystals may be collected at Advanced Photon Source beam line 221D, using a MAR300 CCD detector. The recorded diffractions may be integrated and scaled using the program HKL2000.

The structure may be phased by molecular replacement (MR) method using program Phaser. For example, the MR search model is a Fab subunit derived from a crystal structure of HGFA/Fab complex (PDB code: 2R0L). The CD3ε peptide is built into the structure based on a Fo-Fc map. The structure may be subsequently refined with programs REFMACS and PHENIX using the maximum likelihood target functions, anisotropic individual B-factor refinement method, and TLS refinement method, to achieve convergence.

In one embodiment, the CD3 binding domain of the anti-HER2 TDB comprises the hypervariable regions (HVRs) (a) HVR-H1 comprising the amino acid sequence of SEQ ID NO:84 (b) HVR-H2 comprising the amino acid sequence of SEQ ID NO:85; (c) HVR-H3 comprising the amino acid sequence of SEQ ID NO:86; (d) HVR-L1 comprising the amino acid sequence of SEQ ID NO:69; (e) HVR-L2 comprising the amino acid sequence of SEQ ID NO:87, and (f) HVR-L3 comprising the amino acid sequence of SEQ ID NO:88.

In one embodiment, the CD3 binding domain of the anti-HER2 TDB comprises (a) HVR-H1 comprising the amino acid sequence of SEQ ID NO:66; (b) HVR-H2 comprising the amino acid sequence of SEQ ID NO:67; (c) HVR-H3 comprising the amino acid sequence of SEQ ID NO:68; (d) HVR-L1 comprising the amino acid sequence of SEQ ID NO:69; (e) HVR-L2 comprising the amino acid sequence of SEQ ID NO:70, and (f) HVR-L3 comprising the amino acid sequence of SEQ ID NO:71.

In one embodiment, the CD3 binding domain comprises a heavy chain variable (VH) domain including an amino acid sequence having at least 90% sequence identity (e.g., at least 91%, 92%, 93%, 94%, 95%, 96%, 97%, 98%, or 99% sequence identity) to, or the sequence of, SEQ ID NO:77 and a light chain variable (VL) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO:78. In one embodiment, the CD3 binding domain comprises a VH domain comprising the amino acid sequence of SEQ ID NO:77 and a VL domain comprising the amino acid sequence of SEQ ID NO:78. In a particular instance, the CD3 binding domain can be 40G5c, or a derivative or clonal relative thereof.

In one embodiment, the CD3 binding domain of the anti-HER2 TDB comprises the hypervariable regions (HVRs) (a) HVR-H1 comprising the amino acid sequence of SEQ ID NO:72; (b) HVR-H2 comprising the amino acid sequence of SEQ ID NO:73; (c) HVR-H3 comprising the amino acid sequence of SEQ ID NO:74; (d) HVR-L1 comprising the amino acid sequence of SEQ ID NO:69; (e) HVR-L2 comprising the amino acid sequence of SEQ ID NO:75; and (f) HVR-L3 comprising the amino acid sequence of SEQ ID NO:76.

In one embodiment, the CD3 binding domain comprises a heavy chain variable (VH) domain including an amino acid sequence having at least 90% sequence identity (e.g., at least 91%, 92%, 93%, 94%, 95%, 96%, 97%, 98%, or 99% sequence identity) to, or the sequence of, SEQ ID NO:79 and a light chain variable (VL) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO:80. In one embodiment, the CD3 binding domain comprises a VH domain comprising the amino acid sequence of SEQ ID NO:79 and a VL domain comprising the amino acid sequence of SEQ ID NO:80. In a particular instance, the CD3 binding domain can be 38E4v1, or a derivative or clonal relative thereof.

In one embodiment, the CD3 binding domain of the anti-HER2 TDB comprises the hypervariable regions (HVRs) (a) HVR-H1 comprising the amino acid sequence of SEQ ID NO:72; (b) HVR-H2 comprising the amino acid sequence of SEQ ID NO:73; (c) HVR-H3 comprising the amino acid sequence of SEQ ID NO:74; (d) HVR-L1 comprising the amino acid sequence of SEQ ID NO:69; (e) HVR-L2 comprising the amino acid sequence of SEQ ID NO:75; and (f) HVR-L3 comprising the amino acid sequence of SEQ ID NO:71.

In one embodiment, the CD3 binding domain comprises a heavy chain variable (VH) domain including an amino acid sequence having at least 90% sequence identity (e.g., at least 91%, 92%, 93%, 94%, 95%, 96%, 97%, 98%, or 99% sequence identity) to, or the sequence of, SEQ ID NO:79 and a light chain variable (VL) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO:81. In one embodiment, the CD3 binding domain comprises a VH domain comprising the amino acid sequence of SEQ ID NO:79 and a VL domain comprising the amino acid sequence of SEQ ID NO:81. In a particular instance, the CD3 binding domain can be 38E4v11, or a derivative or clonal relative thereof.

In one aspect, the anti-HER2 TDB comprises (i) a HER2 binding domain comprising (a) a light chain variable domain (VL) comprising the amino acid sequence of SEQ ID NO:1 and (b) a heavy chain variable domain (VH) comprising the amino acid sequence of SEQ ID NO:2 wherein the light chain variable domain and the heavy chain variable domain comprise amino acid substitutions at one or more positions selected from the group consisting of N30(VL) and T31 (VL), both of SEQ ID NO: 1, and N54(VH), G55(VH), D98(VH) and G99 (VH), all of SEQ ID NO:2, numbered according to the Kabat numbering system and (ii) a CD3 binding domain comprising (c) a light chain variable domain (VL) comprising the amino acid sequence of SEQ ID NO:77 and (d) a heavy chain variable domain (VH) comprising the amino acid sequence of SEQ ID NO:78.

In one aspect, the anti-HER2 TDB comprises (i) a HER2 binding domain comprising (a) a light chain variable domain (VL) comprising the amino acid sequence of SEQ ID NO:1 and (b) a heavy chain variable domain (VH) comprising the amino acid sequence of SEQ ID NO:2 wherein the light chain variable domain and the heavy chain variable domain comprise amino acid substitutions at one or more positions selected from the group consisting of N30(VL) and T31 (VL), both of SEQ ID NO: 1, and N54(VH), G55(VH), D98(VH) and G99 (VH), all of SEQ ID NO:2, numbered according to the Kabat numbering system and (ii) a CD3 binding domain comprising (c) a light chain variable domain (VL) comprising the amino acid sequence of SEQ ID NO:79 and (d) a heavy chain variable domain (VH) comprising the amino acid sequence of SEQ ID NO:80.

In one embodiment, the anti-HER2 TDB comprises (i) a HER2 binding domain comprising (a) a light chain variable domain (VL) comprising the amino acid sequence of SEQ ID NO: 3 and (b) a heavy chain variable domain (VH) comprising the amino acid sequence of SEQ ID NO: 4 and (ii) a CD3 binding domain comprising (c) a light chain variable domain (VL) comprising the amino acid sequence of SEQ ID NO:77 and (d) a heavy chain variable domain (VH) comprising the amino acid sequence of SEQ ID NO:78.

In one embodiment, the anti-HER2 TDB comprises (i) a HER2 binding domain comprising (a) a light chain variable domain (VL) comprising the amino acid sequence of SEQ ID NO: 3 and (b) a heavy chain variable domain (VH) comprising the amino acid sequence of SEQ ID NO: 4 and (ii) a CD3 binding domain comprising (c) a light chain variable domain (VL) comprising the amino acid sequence of SEQ ID NO:79 and (d) a heavy chain variable domain (VH) comprising the amino acid sequence of SEQ ID NO:80.

In one embodiment, the anti-HER2 TDB comprises (i) a HER2 binding domain comprising (a) a light chain variable domain (VL) comprising the amino acid sequence of SEQ ID NO: 3 and (b) a heavy chain variable domain (VH) comprising the amino acid sequence of SEQ ID NO: 5 and (ii) a CD3 binding domain comprising (c) a light chain variable domain (VL) comprising the amino acid sequence of SEQ ID NO:77 and (d) a heavy chain variable domain (VH) comprising the amino acid sequence of SEQ ID NO:78.

In one embodiment, the anti-HER2 TDB comprises (i) a HER2 binding domain comprising (a) a light chain variable domain (VL) comprising the amino acid sequence of SEQ ID NO: 3 and (b) a heavy chain variable domain (VH) comprising the amino acid sequence of SEQ ID NO: 5 and (ii) a CD3 binding domain comprising (c) a light chain variable domain (VL) comprising the amino acid sequence of SEQ ID NO:79 and (d) a heavy chain variable domain (VH) comprising the amino acid sequence of SEQ ID NO:80.

In one embodiment, the anti-HER2 TDB comprises (i) a HER2 binding domain comprising (a) an HVR-H1 comprising the amino acid sequence of SEQ ID NO:50; (b) an HVR-H2 comprising the amino acid sequence of SEQ ID NO:57; (c) an HVR-H3 comprising the amino acid sequence of SEQ ID NO:62; (d) an HVR-L1 comprising the amino acid sequence of SEQ ID NO: 53; (e) an HVR-L2 comprising the amino acid sequence of SEQ ID NO:48; and (f) an HVR-L3 comprising the amino acid sequence of SEQ ID NO:49; and (ii) a CD3 binding domain comprising: (a) HVR-H1 comprising the amino acid sequence of SEQ ID NO:66; (b) HVR-H2 comprising the amino acid sequence of SEQ ID NO:67; (c) HVR-H3 comprising the amino acid sequence of SEQ ID NO:68; (d) HVR-L1 comprising the amino acid sequence of SEQ ID NO:69; (e) HVR-L2 comprising the amino acid sequence of SEQ ID NO:70; and (f) HVR-L3 comprising the amino acid sequence of SEQ ID NO:71. In some embodiments, the anti-HER2 antibody comprises a HER2 binding domain comprising a heavy chain variable region comprising the sequence of SEQ ID NO:7 and a light chain variable region comprising the sequence of SEQ ID NO:6.

In one embodiment, the anti-HER2 TDB comprises (i) a HER2 binding domain comprising (a) an HVR-H1 comprising the amino acid sequence of SEQ ID NO:50; (b) an HVR-H2 comprising the amino acid sequence of SEQ ID NO:57; (c) an HVR-H3 comprising the amino acid sequence of SEQ ID NO:63; (d) an HVR-L1 comprising the amino acid sequence of SEQ ID NO: 54; (e) an HVR-L2 comprising the amino acid sequence of SEQ ID NO:48; and (f) an HVR-L3 comprising the amino acid sequence of SEQ ID NO:49; and (ii) a CD3 binding domain comprising: (a) HVR-H1 comprising the amino acid sequence of SEQ ID NO:66; (b) HVR-H2 comprising the amino acid sequence of SEQ ID NO:67; (c) HVR-H3 comprising the amino acid sequence of SEQ ID NO:68; (d) HVR-L1 comprising the amino acid sequence of SEQ ID NO:69; (e) HVR-L2 comprising the amino acid sequence of SEQ ID NO:70; and (f) HVR-L3 comprising the amino acid sequence of SEQ ID NO:71. In some embodiments, the anti-HER2 antibody comprises a HER2 binding domain comprising a heavy chain variable region comprising the sequence of SEQ ID NO:9 and a light chain variable region comprising the sequence of SEQ ID NO:8.

In one embodiment, the anti-HER2 TDB comprises (i) a HER2 binding domain comprising (a) an HVR-H1 comprising the amino acid sequence of SEQ ID NO:50; (b) an HVR-H2 comprising the amino acid sequence of SEQ ID NO:58; (c) an HVR-H3 comprising the amino acid sequence of SEQ ID NO:63; (d) an HVR-L1 comprising the amino acid sequence of SEQ ID NO: 54; (e) an HVR-L2 comprising the amino acid sequence of SEQ ID NO:48; and (f) an HVR-L3 comprising the amino acid sequence of SEQ ID NO:49; and (ii) a CD3 binding domain comprising: (a) HVR-H1 comprising the amino acid sequence of SEQ ID NO:66; (b) HVR-H2 comprising the amino acid sequence of SEQ ID NO:67; (c) HVR-H3 comprising the amino acid sequence of SEQ ID NO:68; (d) HVR-L1 comprising the amino acid sequence of SEQ ID NO:69; (e) HVR-L2 comprising the amino acid sequence of SEQ ID NO:70; and (f) HVR-L3 comprising the amino acid sequence of SEQ ID NO:71. In some embodiments, the anti-HER2 antibody comprises a HER2 binding domain comprising a heavy chain variable region comprising the sequence of SEQ ID NO:11 and a light chain variable region comprising the sequence of SEQ ID NO:10.

In one embodiment, the anti-HER2 TDB comprises (i) a HER2 binding domain comprising (a) an HVR-H1 comprising the amino acid sequence of SEQ ID NO:50; (b) an HVR-H2 comprising the amino acid sequence of SEQ ID NO:51; (c) an HVR-H3 comprising the amino acid sequence of SEQ ID NO:62; (d) an HVR-L1 comprising the amino acid sequence of SEQ ID NO: 54; (e) an HVR-L2 comprising the amino acid sequence of SEQ ID NO:48; and (f) an HVR-L3 comprising the amino acid sequence of SEQ ID NO:49; and (ii) a CD3 binding domain comprising: (a) HVR-H1 comprising the amino acid sequence of SEQ ID NO:66; (b) HVR-H2 comprising the amino acid sequence of SEQ ID NO:67; (c) HVR-H3 comprising the amino acid sequence of SEQ ID NO:68; (d) HVR-L1 comprising the amino acid sequence of SEQ ID NO:69; (e) HVR-L2 comprising the amino acid sequence of SEQ ID NO:70; and (f) HVR-L3 comprising the amino acid sequence of SEQ ID NO:71. In some embodiments, the anti-HER2 antibody comprises a HER2 binding domain comprising a heavy chain variable region comprising the sequence of SEQ ID NO:13 and a light chain variable region comprising the sequence of SEQ ID NO:12.

In one embodiment, the anti-HER2 TDB comprises (i) a HER2 binding domain comprising (a) an HVR-H1 comprising the amino acid sequence of SEQ ID NO:50; (b) an HVR-H2 comprising the amino acid sequence of SEQ ID NO:58; (c) an HVR-H3 comprising the amino acid sequence of SEQ ID NO:63; (d) an HVR-L1 comprising the amino acid sequence of SEQ ID NO: 55; (e) an HVR-L2 comprising the amino acid sequence of SEQ ID NO:48; and (f) an HVR-L3 comprising the amino acid sequence of SEQ ID NO:49; and (ii) a CD3 binding domain comprising: (a) HVR-H1 comprising the amino acid sequence of SEQ ID NO:66; (b) HVR-H2 comprising the amino acid sequence of SEQ ID NO:67; (c) HVR-H3 comprising the amino acid sequence of SEQ ID NO:68; (d) HVR-L1 comprising the amino acid sequence of SEQ ID NO:69; (e) HVR-L2 comprising the amino acid sequence of SEQ ID NO:70; and (f) HVR-L3 comprising the amino acid sequence of SEQ ID NO:71.

In one embodiment, the anti-HER2 TDB comprises (a) an HVR-H1 comprising the amino acid sequence of SEQ ID NO:50; (b) an HVR-H2 comprising the amino acid sequence of SEQ ID NO:51; (c) an HVR-H3 comprising the amino acid sequence of SEQ ID NO:63; (d) an HVR-L1 comprising the amino acid sequence of SEQ ID NO: 54; (e) an HVR-L2 comprising the amino acid sequence of SEQ ID NO:48; and (f) an HVR-L3 comprising the amino acid sequence of SEQ ID NO:49; and (ii) a CD3 binding domain comprising: (a) HVR-H1 comprising the amino acid sequence of SEQ ID NO:66; (b) HVR-H2 comprising the amino acid sequence of SEQ ID NO:67; (c) HVR-H3 comprising the amino acid sequence of SEQ ID NO:68; (d) HVR-L1 comprising the amino acid sequence of SEQ ID NO:69; (e) HVR-L2 comprising the amino acid sequence of SEQ ID NO:70; and (f) HVR-L3 comprising the amino acid sequence of SEQ ID NO:71.

In one embodiment, the anti-HER2 TDB comprises: (a) an HVR-H1 comprising the amino acid sequence of SEQ ID NO:50; (b) an HVR-H2 comprising the amino acid sequence of SEQ ID NO:51; (c) an HVR-H3 comprising the amino acid sequence of SEQ ID NO:65; (d) an HVR-L1 comprising the amino acid sequence of SEQ ID NO:54; (e) an HVR-L2 comprising the amino acid sequence of SEQ ID NO:48; and (f) an HVR-L3 comprising the amino acid sequence of SEQ ID NO:49; and (ii) a CD3 binding domain comprising: (a) HVR-H1 comprising the amino acid sequence of SEQ ID NO:66; (b) HVR-H2 comprising the amino acid sequence of SEQ ID NO:67; (c) HVR-H3 comprising the amino acid sequence of SEQ ID NO:68; (d) HVR-L1 comprising the amino acid sequence of SEQ ID NO:69; (e) HVR-L2 comprising the amino acid sequence of SEQ ID NO:70; and (f) HVR-L3 comprising the amino acid sequence of SEQ ID NO:71.

In one embodiment, the anti-HER2 TDB comprises: (a) an HVR-H1 comprising the amino acid sequence of SEQ ID NO:50; (b) an HVR-H2 comprising the amino acid sequence of SEQ ID NO:58; (c) an HVR-H3 comprising the amino acid sequence of SEQ ID NO:63; (d) an HVR-L1 comprising the amino acid sequence of SEQ ID NO:53; (e) an HVR-L2 comprising the amino acid sequence of SEQ ID NO:48; and (f) an HVR-L3 comprising the amino acid sequence of SEQ ID NO:49; and (ii) a CD3 binding domain comprising: (a) HVR-H1 comprising the amino acid sequence of SEQ ID NO:66; (b) HVR-H2 comprising the amino acid sequence of SEQ ID NO:67; (c) HVR-H3 comprising the amino acid sequence of SEQ ID NO:68; (d) HVR-L1 comprising the amino acid sequence of SEQ ID NO:69; (e) HVR-L2 comprising the amino acid sequence of SEQ ID NO:70; and (f) HVR-L3 comprising the amino acid sequence of SEQ ID NO:71.

In one embodiment, the anti-HER2 TDB comprises: (a) an HVR-H1 comprising the amino acid sequence of SEQ ID NO:50; (b) an HVR-H2 comprising the amino acid sequence of SEQ ID NO:58; (c) an HVR-H3 comprising the amino acid sequence of SEQ ID NO:63; (d) an HVR-L1 comprising the amino acid sequence of SEQ ID NO:55; (e) an HVR-L2 comprising the amino acid sequence of SEQ ID NO:48; and (f) an HVR-L3 comprising the amino acid sequence of SEQ ID NO:49; and (ii) a CD3 binding domain comprising: (a) HVR-H1 comprising the amino acid sequence of SEQ ID NO:66; (b) HVR-H2 comprising the amino acid sequence of SEQ ID NO:67; (c) HVR-H3 comprising the amino acid sequence of SEQ ID NO:68; (d) HVR-L1 comprising the amino acid sequence of SEQ ID NO:69; (e) HVR-L2 comprising the amino acid sequence of SEQ ID NO:70; and (f) HVR-L3 comprising the amino acid sequence of SEQ ID NO:71.

In a further aspect, an anti-HER2 antibody according to any of the above embodiments may incorporate any of the features, singly or in combination, as described in Sections 1-7 below.

1. Antibody Affinity

In certain embodiments, an antibody provided herein has a dissociation constant (Kd) of $\leq 1$ μM, $\leq 100$ nM, $\leq 10$ nM, $\leq 1$ nM, $\leq 0.1$ nM, $\leq 0.01$ nM, or $\leq 0.001$ nM (e.g., $10^{-8}$ M or less, e.g., from $10^{-8}$ M to $10^{-13}$ M, e.g., from $10^{-9}$ M to $10^{-13}$ M).

In one embodiment, Kd is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 μl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using a BIACORE® surface plasmon resonance assay. For example, an assay using a BIACORE®-2000 or a BIACORE®-3000 (BIAcore, Inc., Piscataway, N.J.) is performed at 25° C. with immobilized antigen CM5 chips at ~10 response units (RU). In one embodiment, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 μl/min. Association rates ($k_o$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{on}/k_{off}$. See, for example, Chen et al., *J. Mol. Biol.* 293:865-881 (1999). If the on-rate exceeds $10^6 M^{-1} s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. Nat. Med. 9:129-134 (2003). For a review of scFv fragments, see, e.g., Pluckthün, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al. Nat. Med. 9:129-134 (2003); and Hollinger et al. Proc. Natl. Acad. Sci. USA 90: 6444-6448 (1993). Triabodies and tetrabodies are also described in Hudson et al. Nat. Med. 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. E. coli or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al. Proc. Natl. Acad. Sci. USA, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing specificity determining region (SDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

Human framework regions that may be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol., 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., J. Biol. Chem. 272:10678-10684 (1997) and Rosok et al., J. Biol. Chem. 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, Curr. Opin. Pharmacol. 5: 368-74 (2001) and Lon berg, Curr. Opin. Immunol. 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., U.S. Pat. Nos. 6,075,181 and 6,150,584 describing XENO-MOUSE™ technology; U.S. Pat. No. 5,770,429 describing HuMAB® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor J. Immunol., 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991).) Human antibodies generated via human B-cell hybridoma technology are also described in Li et al., Proc. Natl. Acad, Sci USA, 103:3557-3562 (2006).

Additional methods include those described, for example, in U.S. Pat. No. 7,189,826 (describing production of monoclonal human IgM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an anti-HER2 antibody provided herein is a multispecific antibody, e.g. a bispecific antibody. Multispecific antibodies are monoclonal antibodies that have binding specificities for at least two different sites. In certain embodiments, one of the binding specificities is for HER2 and the other is for any other antigen. In certain embodiments, bispecific antibodies may bind to two different epitopes of HER2. Bispecific antibodies may also be used to localize cytotoxic agents to cells which express HER2. Bispecific antibodies can be prepared as full length antibodies or antibody fragments. In certain embodiments, the multispecific antibody is a TDB as described above.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). "Knob-in-hole" engineering of multispecific antibodies may be utilized to generate a first arm containing a knob and a second arm containing the hole into which the knob of the first arm may bind. The knob of the multispecific antibodies of the invention may be an anti-CD3 arm in one embodiment. Alternatively, the knob of the multispecific antibodies of the invention may be an anti-target/antigen arm in one embodiment, such as the anti-HER2 arm. The hole of the multispecific antibodies of the invention may be an anti-CD3 arm in one embodiment. Alternatively, the hole of the multispecific antibodies of the invention may be an anti-target/antigen arm, such as an anti-HER2 arm, in one embodiment. Multispecific antibodies may also be engineered using immunoglobulin crossover (also known as Fab domain exchange or CrossMab format) technology (see eg., WO2009/080253; Schaefer et al., *Proc. Natl. Acad. Sci. USA,* 108:11187-11192 (2011)). Multispecific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g. Gruber et al., *J. Immunol.,* 152:5368 (1994)); and preparing trispecific antibodies as described, e.g., in Tutt et al. *J. Immunol.* 147: 60 (1991). Multi-specific antibodies can be generated using a bis Fab format (see, eg WO2011069104).

Engineered antibodies with three or more functional antigen binding sites, including "Octopus antibodies," are also included herein (see, e.g. US 2006/0025576A1).

The antibodies, or antibody fragments thereof, may also include a "Dual Acting FAb" or "DAF" comprising an antigen binding site that binds to CD3 as well as another, different antigen (e.g., a second biological molecule) (see, e.g., US 2008/0069820).

7. Antibody Variants

In certain embodiments, amino acid sequence variants of the anti-HER2 antibodies of the invention are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, for example, antigen-binding.

a. Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 2 under the heading of "preferred substitutions." More substantial changes are provided in Table 2 under the heading of "exemplary substitutions," and as further described below in reference to amino acid side chain classes. Amino acid substitutions may be introduced into an antibody of interest and the products screened for a desired activity, for example, retained/improved antigen binding, decreased immunogenicity, or improved ADCC or CDC.

TABLE 2

Exemplary and Preferred Amino Acid Substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or residues that contact antigen, with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b. Glycosylation Variants

In certain embodiments, anti-HER2 antibodies of the invention can be altered to increase or decrease the extent to which the antibody is glycosylated. Addition or deletion of glycosylation sites to anti-HER2 antibody of the invention may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, anti-HER2 antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Anti-HER2 antibodies variants are further provided with bisected oligosaccharides, for example, in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c. Fc Region Variants

In certain embodiments, one or more amino acid modifications may be introduced into the Fc region of an anti-HER2 antibody of the invention, thereby generating an Fc region variant (see e.g., US 2012/0251531). The Fc region variant may comprise a human Fc region sequence (e.g., a human IgG1, IgG2, IgG3 or IgG4 Fc region) comprising an amino acid modification (e.g., a substitution) at one or more amino acid positions.

In certain embodiments, the invention contemplates an anti-HER2 antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al. *J. Immunol. Methods* 202:163 (1996); Cragg, M. S. et al. *Blood.* 101:1045-1052 (2003); and Cragg, M. S. and M. J. Glennie *Blood.* 103:2738-2743 (2004)). FcRn binding and in vivo clearance/half life determinations can also be performed using methods known in the art (see, e.g., Petkova, S. B. et al. *Intl. Immunol.* 18(12):1759-1769 (2006)).

Antibodies with reduced effector function include those with substitution of one or more of Fc region residues 238, 265, 269, 270, 297, 327 and 329 (U.S. Pat. Nos. 6,737,056 and 8,219,149). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. Nos. 7,332,581 and 8,219,149).

In certain embodiments, the proline at position 329 of a wild-type human Fc region in the antibody is substituted with glycine or arginine or an amino acid residue large enough to destroy the proline sandwich within the Fc/Fc.gamma. receptor interface that is formed between the proline 329 of the Fc and the tryptophan residues Trp 87 and Trp 110 of FcgRIII (Sondermann et al.: *Nature* 406, 267-273 (20 Jul. 2000)). In certain embodiments, the antibody comprises at least one further amino acid substitution. In one embodiment, the further amino acid substitution is S228P, E233P, L234A, L235A, L235E, N297A, N297D, or P331S, and still in another embodiment the at least one further amino acid substitution is L234A and L235A of the human IgG1 Fc region or S228P and L235E of the human IgG4 Fc region (see e.g., US 2012/0251531), and still in another embodiment the at least one further amino acid substitution is L234A and L235A and P329G of the human IgG1 Fc region.

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

In some aspects the anti-HER2 antibody comprises an Fc region comprising an N297G mutation.

In some embodiments, the anti-HER2 antibody comprising the N297G mutation comprises one or more heavy chain constant domains, wherein the one or more heavy chain constant domains are selected from a first CH1 ($CH1_1$) domain, a first CH2 ($CH2_1$) domain, a first CH3 ($CH3_1$) domain, a second CH1 ($CH1_2$) domain, second CH2 ($CH2_2$) domain, and a second CH3 ($CH3_2$) domain. In some instances, at least one of the one or more heavy chain constant domains is paired with another heavy chain constant domain. In some instances, the $CH3_1$ and $CH3_2$ domains each comprise a protuberance or cavity, and wherein the protuberance or cavity in the $CH3_1$ domain is positionable in the cavity or protuberance, respectively, in the $CH3_2$ domain. In some instances, the $CH3_1$ and $CH3_2$ domains meet at an interface between said protuberance and cavity. In some instances, the $CH2_1$ and $CH2_2$ domains each comprise a protuberance or cavity, and wherein the protuberance or cavity in the $CH2_1$ domain is positionable in the cavity or protuberance, respectively, in the $CH2_2$ domain. In other instances, the $CH2_1$ and $CH2_2$ domains meet at an interface between said protuberance and cavity. In some instances, the anti-HER2 antibody is an IgG1 antibody.

d. Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, for example, in U.S. Pat. No. 7,521,541.

e. Antibody Derivatives

In certain embodiments, an anti-HER2 antibody of the invention provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Anti-HER2 antibodies of the invention may be produced using recombinant methods and compositions, for example, as described in U.S. Pat. No. 4,816,567. In one embodiment, isolated nucleic acid encoding an anti-HER2 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-HER2 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-HER2 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR⁻ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

C. Assays

Anti-HER2 antibodies of the invention provided herein may be identified, screened for, or characterized for their physical/chemical properties and/or biological activities by various assays known in the art.

1. Binding Assays and Other Assays

In one aspect, an anti-HER2 antibody of the invention is tested for its antigen binding activity, for example, by known methods such as ELISA, Western blot, etc.

In another aspect, competition assays may be used to identify an antibody that competes with an anti-HER2 antibody of the invention for binding to HER2.

In an exemplary competition assay, immobilized HER2 is incubated in a solution comprising a first labeled antibody that binds to HER2 and a second unlabeled antibody that is being tested for its ability to compete with the first antibody for binding to HER2. The second antibody may be present in a hybridoma supernatant. As a control, immobilized HER2 is incubated in a solution comprising the first labeled antibody but not the second unlabeled antibody. After incubation under conditions permissive for binding of the first antibody to HER2, excess unbound antibody is removed, and the amount of label associated with immobilized HER2 is measured. If the amount of label associated with immobilized HER2 is substantially reduced in the test sample relative to the control sample, then that indicates that the second antibody is competing with the first antibody for binding to HER2. See, e.g., Harlow and Lane (1988) *Antibodies: A Laboratory Manual*. Ch. 14 (Cold Spring Harbor Laboratory, Cold Spring Harbor, N.Y.).

2. Activity Assays

In one aspect, assays are provided for identifying anti-HER2 antibodies thereof having biological activity. Biological activity may include, for example, binding to HER2, or a peptide fragment thereof, either in vivo, in vitro, or ex vivo. In the case of a multispecific (e.g., bispecific) anti-HER2 antibody of the invention (e.g., a TDB antibody having one anti-CD3 arm and one arm that recognizes HER2), biological activity may also include, for example, effector cell activation (e.g., T cell (e.g., CD8+ and/or CD4+ T cell) activation), effector cell population expansion (i.e., an increase in T cell count), target cell population reduction (i.e., a decrease in the population of cells expressing the second biological molecule on their cell surfaces), and/or target cell killing. Antibodies having such biological activity in vivo and/or in vitro are provided. In certain embodiments, an antibody of the invention is tested for such biological activity, as described in detail in the Examples herein below.

D. Immunoconjugates

The invention also provides immunoconjugates comprising an anti-HER2 antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498, 298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an anti-HER2 antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes.

In another embodiment, an immunoconjugate comprises an anti-HER2 antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, STAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

E. Methods and Compositions for Diagnostics and Detection

In certain embodiments, any of the anti-HER2 antibodies of the invention is useful for detecting the presence of HER2 in a biological sample. The term "detecting" as used herein encompasses quantitative or qualitative detection. In certain embodiments, a biological sample comprises a cell or tissue.

In one embodiment, an anti-HER2 antibody for use in a method of diagnosis or detection is provided. In a further aspect, a method of detecting the presence of HER2 in a biological sample is provided. In certain embodiments, the method comprises contacting the biological sample with an anti-HER2 antibody as described herein under conditions permissive for binding of the anti HER2 antibody to HER2, and detecting whether a complex is formed between the anti-HER2 antibody and HER2. Such method may be an in vitro or in vivo method.

In certain embodiments, labeled anti-HER2 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

Pharmaceutical formulations of an anti-HER2 antibody of the invention are prepared by mixing such antibody having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171, 586 and WO2006/044908, the latter formulations including a histidine-acetate buffer.

The formulation herein may also contain more than one active ingredients as necessary for the particular indication being treated, preferably those with complementary activities that do not adversely affect each other. For example, it may be desirable to further provide an additional therapeutic agent (e.g., a chemotherapeutic agent, a cytotoxic agent, a growth inhibitory agent, and/or an anti-hormonal agent, such as those recited herein above). Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, for example, films, or microcapsules.

The formulations to be used for in vivo administration are generally sterile. Sterility may be readily accomplished, e.g., by filtration through sterile filtration membranes.

G. Therapeutic Methods and Compositions

Any of the anti-HER2 antibodies (including anti-HER2 TDBs) of the invention may be used in therapeutic methods.

In one aspect, an anti-HER2 antibody for use as a medicament is provided. In further aspects, an anti-HER2 antibody for use in treating or delaying progression of a cell proliferative disorder (e.g., cancer, such as a HER positive cancer) is provided. In certain embodiments, an anti-HER2 antibody for use in a method of treatment is provided. In certain embodiments, the invention provides an anti-HER2 antibody for use in a method of treating an individual having a cell proliferative disorder comprising administering to the individual an effective amount of the anti-HER2 antibody. In one embodiment, the method further comprises administering to the individual an effective amount of at least one additional therapeutic agent, for example, as described below. In further embodiments, the invention provides an anti-HER2 antibody (such as a anti-HER2 TDB) for use in enhancing immune function in an individual having a cell proliferative disorderr. In certain embodiments, the invention provides an anti-HER2 antibody for use in a method of enhancing immune function in an individual having a cell proliferative disorder comprising administering to the individual an effective of the anti-HER2 antibody to activate effector cells (e.g., T cells, e.g., CD8+ and/or CD4+ T cells), expand (increase) an effector cell population, reduce a target cell (e.g., a cell expressing a second biological molecule recognized by an anti-HER2 antibody of the invention, such as a bispecific TDB antibody of the invention) population, and/or kill a target cell (e.g., target tumor cell). An "individual" according to any of the above embodiments may be a human.

In a further aspect, the invention provides for the use of an anti-HER2 antibody in the manufacture or preparation of a medicament. In one embodiment, the medicament is for treatment of a cell proliferative disorder (e.g., cancer). In a further embodiment, the medicament is for use in a method of treating a cell proliferative disorder comprising administering to an individual having a cell proliferative disorder an effective amount of the medicament. In one such embodiment, the method further comprises administering to the individual an effective amount of at least one additional therapeutic agent, for example, as described below. In a further embodiment, the medicament is for activating effector cells (e.g., T cells, e.g., CD8+ and/or CD4+ T cells), expanding (increasing) an effector cell population, reducing a target cell (e.g., a cell expressing a second biological molecule recognized by an anti-HER2 antibody of the invention, such as a bispecific TDB antibody of the invention) population, and/or killing target cells (e.g., target tumor cells) in the individual. In a further embodiment, the medicament is for use in a method of enhancing immune function in an individual having a cell proliferative disorder comprising administering to the individual an amount effective of the medicament to activate effector cells (e.g., T cells, e.g., CD8+ and/or CD4+ T cells), expand (increase) an effector cell population, reduce a target cell (e.g., a cell expressing a second biological molecule recognized by an anti-HER2 antibody of the invention, such as a bispecific TDB antibody of the invention) population, and/or kill a target cell (e.g., target tumor cell). An "individual" according to any of the above embodiments may be a human.

In a further aspect, the invention provides a method for treating a cell proliferative disorder (e.g., cancer). In one embodiment, the method comprises administering to an individual having such a cell proliferative disorder an effective amount of an anti-HER2 antibody. In one such embodiment, the method further comprises administering to the individual an effective amount of at least one additional therapeutic agent, for example, as described below. An "individual" according to any of the above embodiments may be a human.

In a further aspect, the invention provides a method for enhancing immune function in an individual having a cell proliferative disorder in an individual having a cell proliferative disorder. In one embodiment, the method comprises administering to the individual an effective amount of an anti-HER2 antibody to activate effector cells (e.g., T cells, e.g., CD8+ and/or CD4+ T cells), expand (increase) an effector cell population, reduce a target cell (e.g., a cell expressing a second biological molecule recognized by an anti-HER2 antibody of the invention, such as a bispecific TDB antibody of the invention) population, and/or kill a target cell (e.g., target tumor cell). In one embodiment, an "individual" is a human.

In a further aspect, the invention provides a method for treating a cancer which expresses HER2, including HER2-positive cancers. In one embodiment, the method comprises administering to an individual having such a cancer an effective amount of an anti-HER2 antibody of the invention. In one embodiment, the anti-HER2 antibody is a monospecific bivalent antibody. In another embodiment, the anti-HER2 antibody is a bispecific TDB antibody with an anti-HER2 targeting arm and an anti-CD3 targeting arm. In a preferred embodiment, the HER2-TDB possesses an acceptable toxicity profile when administered in an effective dose in a patient. In one embodiment, the CD3 arm of the HER2-TDB with an acceptable toxicity profile is a low affinity CD3 arm. In one embodiment, the CD3 arm of the HER2-TDB with an acceptable toxicity profile is 40G5c.

Antibodies of the invention can be used either alone or in combination with other agents in a therapy. For instance, an antibody of the invention may be co-administered with at least one additional therapeutic agent. In certain embodiments, an additional therapeutic agent is a chemotherapeutic agent, growth inhibitory agent, cytotoxic agent, agent used in radiation therapy, anti-angiogenesis agent, apoptotic agent, anti-tubulin agent, or other agent, such as a epidermal growth factor receptor (EGFR) antagonist (e.g., a tyrosine kinase inhibitor), HER1/EGFR inhibitor (e.g., erlotinib (Tarceva™), platelet derived growth factor inhibitor (e.g., Gleevec™ (Imatinib Mesylate)), a COX-2 inhibitor (e.g., celecoxib), interferon, cytokine, antibody other than the anti-HER2 antibody of the invention, such as an antibody that bind to one or more of the following targets ErbB2, ErbB3, ErbB4, PDGFR-beta, BlyS, APRIL, BCMA VEGF, or VEGF receptor(s), TRAIL/Apo2, PD-1, PD-L1, PD-L2, or another bioactive or organic chemical agent.

In some embodiments, the anti-HER2 antibody is administered to the subject in combination with a PD-1 axis binding antagonist or an additional therapeutic agent. In some embodiments, the additional therapeutic agent is administered prior to or subsequent to the administration of the anti-HER2 antibody. In some embodiments, the additional therapeutic agent is administered concurrently with the anti-HER2 antibody. In some embodiments, the PD-1 axis binding antagonist is selected from the group consisting of a PD-1 binding antagonist, a PD-L1 binding antagonist, and a PD-L2 binding antagonist.

In some embodiments, the PD-1 axis binding antagonist is a PD-1 binding antagonist. In some embodiments, the PD-1 binding antagonist is an anti-PD-1 antibody, antigen-binding fragment thereof, immunoadhesin, fusion protein, oligopeptide, or other molecule that decreases, blocks, inhibits, abrogates, or interferes with signal transduction resulting from the interaction of PD-1 with PD-L1 and/or PD-L2. In some embodiments, the PD-1 binding antagonist is an anti-PD-1 antibody. In a specific embodiment, the PD-1 binding antagonist is MDX-1106 (nivolumab). In another specific embodiment, the PD-1 binding antagonist is MK-3475 (pembrolizumab). In another specific embodiment, the PD-1 binding antagonist is CT-011 (pidilizumab). In another specific embodiment, the PD-1 binding antagonist is AMP-224. In another specific embodiment, the PD-1 binding antagonist is MED1-0680. In another specific embodiment, the PD-1 binding antagonist is PDR001. In another specific embodiment, the PD-1 binding antagonist is REGN2810. In another specific embodiment, the PD-1 binding antagonist is BGB-108.

In other embodiments, the PD-1 axis binding antagonist is a PD-L1 binding antagonist. In some embodiments, the PD-L1 binding antagonist is an anti-PD-L1 antibody, antigen binding fragment thereof, immunoadhesin, fusion protein, oligopeptide, or other molecule that decreases, blocks, inhibits, abrogates, or interferes with signal transduction resulting from the interaction of PD-L1 with one or more of its binding partners, such as PD-1, B7-1. In some embodiments, the PD-L1 binding antagonist is an anti-PD-L1 antibody. In still another specific embodiment, the anti-PD-L1 antibody is MPDL3280A (atezolizumab). In a specific embodiment, the anti-PD-L1 antibody is YW243.55.S70. In another specific embodiment, the anti-PD-L1 antibody is MDX-1105. In another specific embodiment, the anti PD-L1 antibody is MSB0015718C. In still another specific embodiment, the anti-PD-L1 antibody is MED14736.

In other embodiments, the PD-1 axis binding antagonist is a PD-L2 binding antagonist. In some embodiments, the PD-L2 binding antagonist is an anti-PD-L2 antibody, antigen binding fragment thereof, immunoadhesin, fusion protein, oligopeptide, or other molecule that decreases, blocks, inhibits, abrogates, or interferes with signal transduction resulting from the interaction of PD-L2 with one or more of its binding partners, such as PD-1. In some embodiments, the PD-L2 binding antagonist is an anti-PD-L2 antibody. In some embodiments, the PD-L2 binding antagonist is an immunoadhesin.

In a preferable embodiment, the HER2-positive cancer is a HER2-positive breast cancer or HER2-positive gastric cancer. In one embodiment, an anti-HER2 antibody is co-administered with one or more additional therapeutic agents that target the HER pathway. In one embodiment, the therapeutic agent that targets the HER pathway is selected from an EGFR inhibitor, a HER2 inhibitor, a HER3 inhibitor, and/or a HER4 inhibitor. In one embodiment, an anti-HER2 antibody is co-administered with one or more additional therapeutic agents selected from trastuzumab (Herceptin®), T-DM1 (Kadcyla®) and pertuzumab (Perjeta®). In one embodiment, an anti-HER2 antibody is co-administered with trastuzumab. In one embodiment, a HER2 TDB is co-administered with T-DM1. In one embodiment, an anti-HER2 antibody is co-administered with pertuzumab. In one embodiment, an anti-HER2 antibody is co-administered with trastuzumab and pertuzumab. In one embodiment, an anti-HER2 antibody is co-administered with T-DM1 and pertuzumab.

In some embodiments, the invention provides a method wherein the additional therapeutic agent is a glucocorticoid. In one embodiment, the glucocorticoid is dexamethasone.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent or agents. In one embodiment, administration of the anti-HER2 antibody and administration of an additional therapeutic agent occur within about one month, or within about one, two or three weeks, or within about one, two, three, four, five, or six days, of each other. Anti-HER2 antibodies of the invention can also be used in combination with radiation therapy.

An antibody of the invention (and/or any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. In some embodiments, the antibody is administered by subcutaneous administration. In some embodiments, an anti-HER2 antibody administered by subcutaneous injection exhibits a less toxic response in a patient than the same anti-HER2 antibody administed by intravenous injection. Dosing can be by any suitable route, for example, by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

As a general proposition, the therapeutically effective amount of the anti-HER2 antibody administered to human will be in the range of about 0.01 to about 100 mg/kg of patient body weight whether by one or more administrations. In some embodiments, the antibody used is about 0.01 to about 45 mg/kg, about 0.01 to about 40 mg/kg, about 0.01 to about 35 mg/kg, about 0.01 to about 30 mg/kg, about 0.01 to about 25 mg/kg, about 0.01 to about 20 mg/kg, about 0.01 to about 15 mg/kg, about 0.01 to about 10 mg/kg, about 0.01 to about 5 mg/kg, or about 0.01 to about 1 mg/kg administered daily, for example. In one embodiment, an anti-HER2 antibody described herein is administered to a human at a dose of about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg or about 1400 mg on day 1 of 21-day cycles. The dose may be administered as a single dose or as multiple doses (e.g., 2 or 3 doses), such as infusions. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg, or 10 mg/kg (or any combination thereof) may be administered to the patient. Such doses may be administered intermittently, for example, every week or every three weeks (e.g., such that the patient receives from about two to about twenty, or, for example, about six doses of the anti-HER2 antibody). An initial higher loading dose, followed by one or more lower doses may be administered. The progress of this therapy is easily monitored by conventional techniques and assays.

In some embodiments, the methods may further comprise an additional therapy. The additional therapy may be radiation therapy, surgery, chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy. In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy may be a separate administration of one or more of the thereapeutic agents described above.

H. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

III. Examples

The following are examples of methods and compositions of the invention. It is understood that various other embodiments may be practiced, given the general description provided above.

Example 1. Generation and Characterization of Anti-HER2 Antibodies

Six amino acid residues of hu4D5, two in the light chain variable region and four in the heavy chain variable region of hu4D5, were selected for mutagenesis:
- LC-Asn30=position X1
- LC-Thr30=position X2
- HC-Asn54=position X3
- HC-Gly55=position X4
- HC-Asp98=position X5
- HC-Gly99=position X6

The residues are shown in the sequence alignment of FIG. 1.

Residues X1-X6 were varied and mutations were introduced by Kunkel site-directed mutagenesis. Kunkel TA. (1985). "Rapid and efficient site-specific mutagenesis without phenotypic selection." (PDF). Proceedings of the National Academy of Sciences USA. 82 (2): 488-92.

Light chain CDR L1 sequence "N30, T31" was mutated to include the following variations: QT, TT, ST, ET, DT, and ND.

Heavy chain CDR H2 "N54, G55" was mutated to: AG, EG, SG, NA.

Heavy chain CDR H3 "D98,G99" was mutated to: EG, TG, SG, DS and DT.

Residue numbers indicated are according to Kabat. (Kabat et al., Sequences of proteins of immunological interest, 5th Ed., Public Health Service, National Institutes of Health, Bethesda, Md. (1991)

Combinations of point mutations were introduced onto purified, single stranded heavy and light chain DNA with wildtype hu4D5 sequence. Selected mutant combinations were expressed as Fabs in HEK293 cells, and purified by protein G affinity chromatography. Each of 23 Fab constructs, including a wild type 4D5 Fab, was isolated and screened for binding to recombinant human Her2 ECD (Human Her2/ErbB2 protein, catalog #10004-HCCH, Sino Biological Inc.).

Monovalent binding affinities were determined by surface plasmon resonance using a Biacore T200 instrument. Lyophilized recombinant HER2 protein was diluted to 2 µg/ml in in acetate buffer pH 5.0. The protein was immobilized at 3 different densities on a series S CM5 sensor chip using an amine coupling kit and manufacturer's protocol from GE Healthcare (BR-1000-50).

Purified anti-HER2 Fabs were diluted in 0.5% P20, HBS-EP running buffer in a concentration series from 1.56 nM-50 nM, and injected at a flow rate of 30 µl/minute over all flow cells using flow cell 1 as a blank reference. Each sample was allowed 3 minutes of association and dissociation, and regeneration after each cycle was achieved by 60-second injections of 50 mM HCL after each cycle.

Kinetic interactions were characterized by simultaneous fitting of ka and kd using a 1:1 Langmuir binding model. FIG. 2.

Example 2. Generation and Characterization of Anti-HER2 Antibodies

Amino acid sequences for variable domains of wildtype huMAb4D5 heavy and light chains were sub-cloned into plasmids containing either WT huIgG Fc, or plasmids containing an Fc region with mutations to make knob or hole variant constructs (Trill, et al., Curr Opin Biotechnol 1995: 553-560). Residue numbers are according to Kabat (Kabat et al., 5th Ed., Public Health Service, National Institutes of Health, Bethesda, Md. (1991)). In order to generate monospecific, bivalent antibodies, an intact full-length IgG1 with two antigen binding domains was produced by transfecting mammalian CHO cells with separate plasmids containing WT-Fc heavy or light chain DNA. Monoclonal antibody was expressed and purified by standard methods. (Liu, et al. MAbs. 2010 September-October; 2(5): 480-499). The 4D5v3 bivalent antibody was produced as above with mutations introduced at specified positions by kunkel mutagenesis. The amino acid sequences for the 4D5v3 antibody are shown in FIG. 1:

| | |
|---|---|
| DTYIH | HVR H1: SEQ ID NO: 50 |
| RIYPTNAYTRYADSVKG | HVR H2: SEQ ID NO: 58 |
| WGGTGFYAMDY | HVR H3: SEQ ID NO: 63 |
| RASQDVSTAVA | HVR L1: SEQ ID NO: 54 |
| SASFLYS | HVR L2: SEQ ID NO: 48 |
| QQHYTTPPT | HVR L3: SEQ ID NO: 49 |
| DSV | EVQLVESGGGLVQPGGSLRLSCAASGFNIK DTYIHWVRQAPGKGLEWVARIYPTNAYTRY AKGRFTISADTSKNTAYLQMNSLRAEDTAV YYCSRWGGTGFYAMDYWGQGTLVTVSS VH: SEQ ID NO: 11 |
| SG | DIQMTQSPSSLSASVGDRVTITCRASQDVS TAVAWYQQKPGKAPKWYSASFLYSGVPSRF SRSGTDFTLTISSLQPEDFATYYCQQHYTT PPTFGQGTKVEIK VL: SEQ ID NO: 10 |

Substitution of amino acids at positions N30, G55, and D98 results in 4D5v3 having increased stability as compared to the wildtype 4D5 due to reduced deamidation or isomerization of the antibody, Affinity of Anti-HER2 Variants The binding affinity of the anti-HER2 4D5v3 bivalent antibody for the HER2 target was determined via Biacore analysis using the conditions described above. FIG. 3 shows the results of the Biacore analysis. 4D5v3 exhibited a binding affinity about 10 fold greater than the binding affinity of the wildtype 4D5. Thus, in addition to have increased stability, 4D5v3 also surprisingly exhibited an increased affinity for the HER2 target.

Example 3. Generation and Characterization of Anti-HER2/CD3 Bispecific Antibodies The utility of certain anti-HER antibodies were tested for their utility in the context of a T cell-targeting therapeutic antibody, also referred to as a "T cell-dependent bispecific" (TDB) antibody. TDB antibodies are capable of simultaneously binding cell surface antigens on T cells (e.g., CD3) and cell surface antigens on tumor cells, thereby enabling the bound T cells to contribute to the destruction of the tumor cells.

Anti-HER2 TDB antibodies having one arm directed to CD3 (40G5C) and one arm directed to the cell surface antigen HER2, The HER2 TDBs were produced as full-length antibodies in the knob-into-hole format as human IgG1 (Atwell et al. J. Mol. Biol. 270: 26-35, 1997). Half antibodies were expressed in either *E. coli* or Chinese hamster ovary (CHO) cells, purified by Protein A-affinity chromatography, and the proper half antibody pairs were annealed in vitro as described previously (Spiess et al. Nat. Biotechnol. 2013). If TDB antibody production was carried out in CHO cells, the antibody included an aglycosylation mutation, for example, at residue N297 (e.g., N297G), such that the TDB antibody was an effector-less variant and unable to initiate antibody-dependent cell-mediated cytotoxicity (ADCC). After annealing, the HER2 TDBs were purified by Hydrophobic Interaction Chromatography (HIC) and characterized by analytical gel filtration, mass spectrometry, and polyacrylamide gel electrophoresis. By these methods, various HER2 TDBs having 40G5C as the anti-CD3 arm was generated.

Affinity of Anti-HER2 TDBs for HER2

Affinity of the anti-HER2/CD3 bispecific antibodies were tested for their affinity for their HER2 target via Biacore analysis using the conditions described above. FIG. 4 shows the results of the Biacore analysis. The TDBs showed a range of binding affinities for HER2 antigen. The 4D5v3, 4D5v21 and 4D5v22 antibodies exhibited binding affinities that were about 10 fold greater than the binding affinity of the wildtype 4D5 TDB.

In Vitro Testing of HER2 TDBs

Human PBMC Isolation and CD8+ Cell Purification

Human PBMCs were separated from blood of healthy volunteers using lymphocyte separation medium Lymphoprep (StemCell Technologies, #07811). CD8+ cells were extracted from PBMC using CD8+ Isolation Kit (Miltenyi, #130-094-156) by negative selection.

In Vitro Cell Killing Assays

SK-BR-3 cells were plated at a density of 10 k cells per well in a black, clear bottom 96 well dish (Corning, #3904) on day 1. Purified CD8+ cells were added on day 2 in an 5:1 E:T ratio. Cells were treated with HER2 TDB variants on day 2 at 1000, 100, 10, 1, 0.1, 0.001, 0.0001, 0.00001 ng/mL or untreated. On day 4 CD8+ cells were removed from the plates and wells were washed 2× with PBS. Cell Titer Glo assay was performed according to manufacturer's instructions (Promega, #G7572) and plates were read.

Analysis of T Cell Activation

Target cells and purified CD8+ T cells were mixed in the presence or absence of the various HER2 TDBs. T cell activation was analyzed by flow cytometry. At the end of the incubation, cells were stained with CD8-FITC (BD Bioscience, #555634) and CD69-PE (BD Bioscience, #555531) and CD25-APC (BD Bioscience, #555434).

Results

Figure 5B:
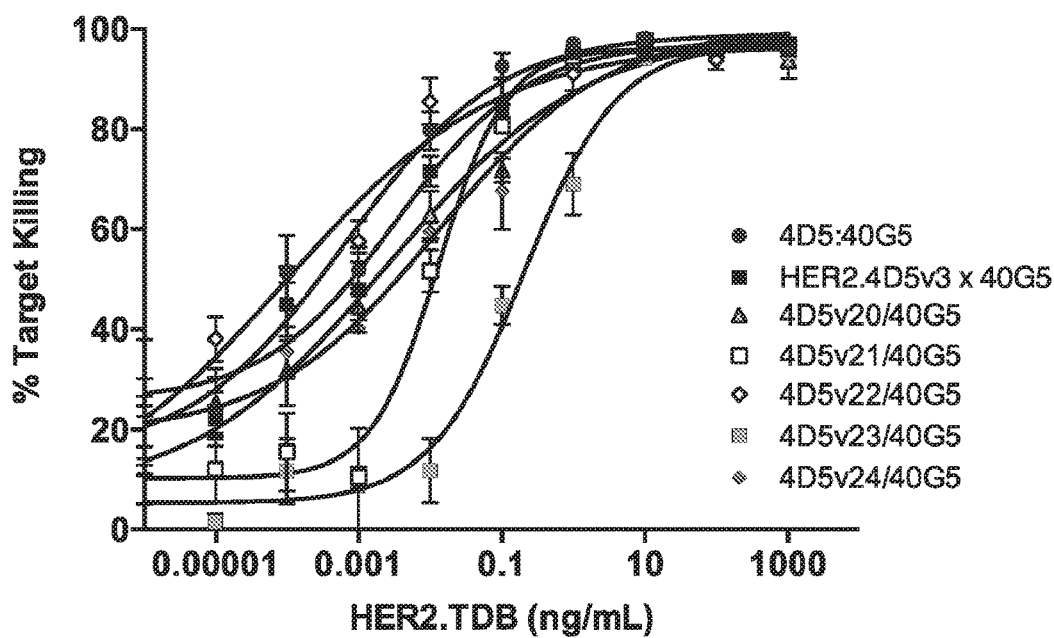
Figure 5C:
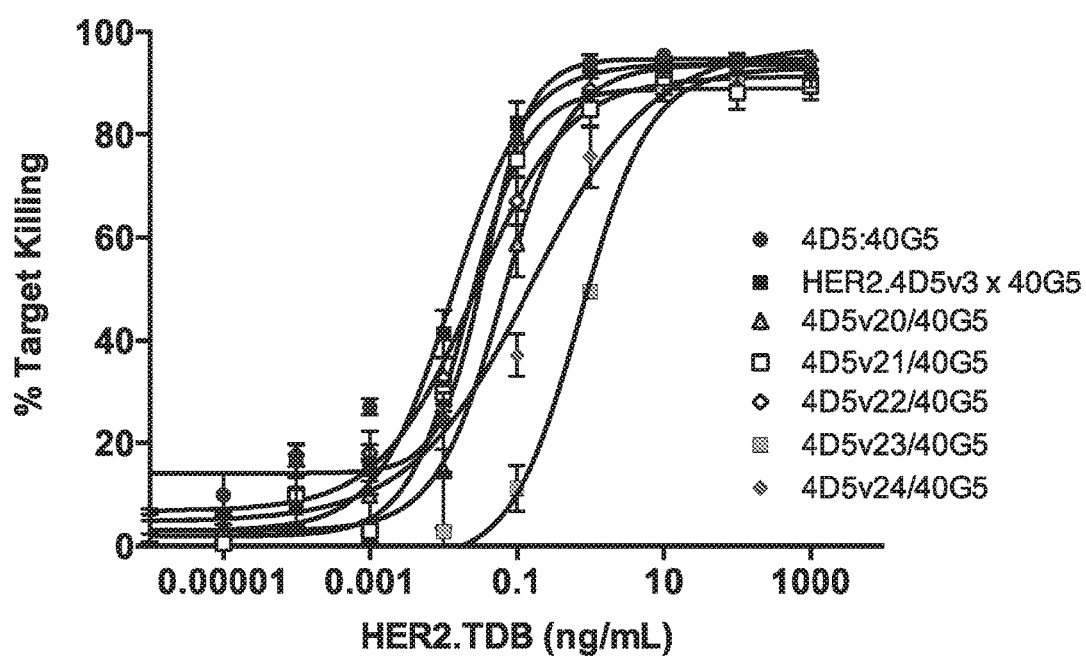

Cell killing assays were performed to evaluate the functional activity of the 4D5-40G5 variants using purified human CD8+ cells and a HER2 expressing target cell line. Variants 20-24 exhibited killing activity similar to both the WT 4D5-40G5 and the 4D5v3-40G5 variants. Of the variants, 4D5v23 was the least potent. The killing assays were repeated with 3 separate donors. The results were similar in each case. FIG. 5A-5C.

Figure 6A:
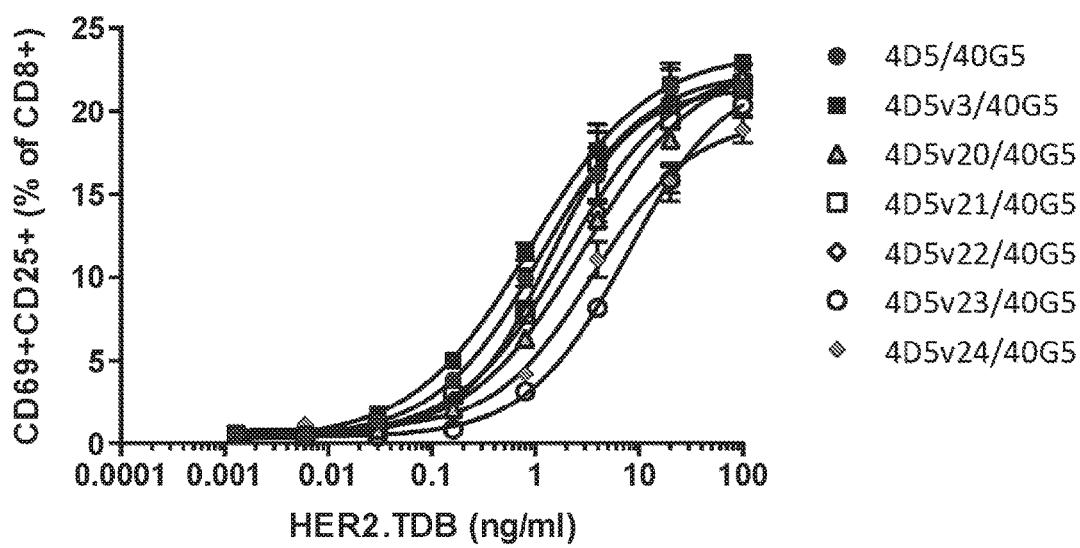
FIGS. 6A and B show the anti-HER2/CD3 TDBs' ability to induce T-cell activity.
Figure 6B:
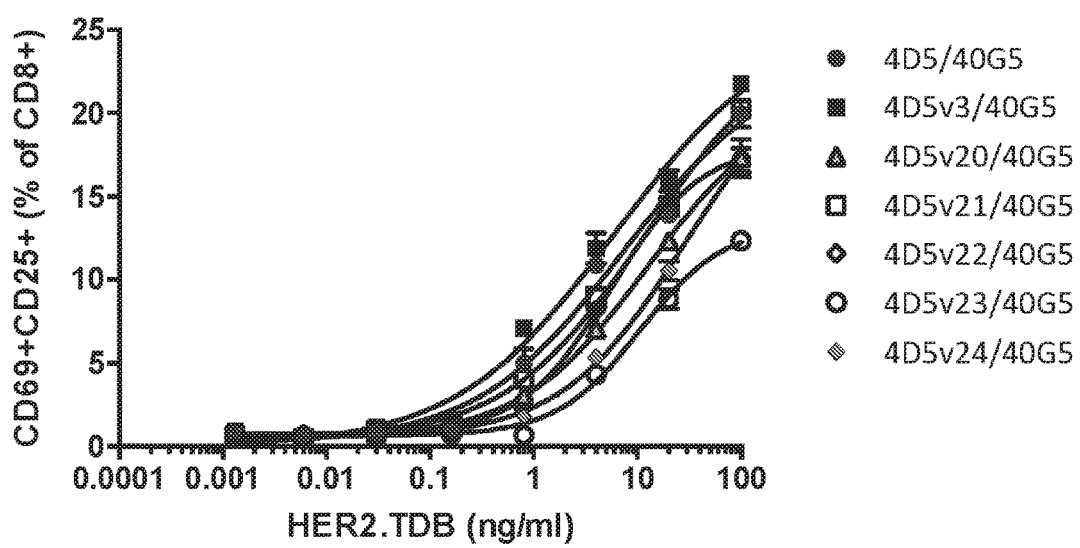

The variants were also tested for their ability to induce T-cell activity. All of the tested variants demonstrated cell activity in assays using cells isolated from from two patients. The T-cell activity results showed consistency with the killing assays with 4D5v 23 as the least activating in CD8+ cells and potent in in vitro killing. In both the killing and in T-cell activation, 4D5v3, 4D5v 20 and 4D5v 24 show the most activity in effectors and higher efficacy against target. FIG. 6

OTHER EMBODIMENTS

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

SEQUENCE LISTING

```
<160> NUMBER OF SEQ ID NOS: 89

<210> SEQ ID NO 1
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95
```

```
Thr Phe Gly Gln Gly Thr Lys Val Glu Ile Lys
            100                 105
```

```
<210> SEQ ID NO 2
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120
```

```
<210> SEQ ID NO 3
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (30)..(30)
<223> OTHER INFORMATION: /replace="Asp" or "Ser" or "Thr" or "Glu" or
      "His" or "Lys" or "Arg" or "Gln"
<220> FEATURE:
<221> NAME/KEY: VARIANT
<222> LOCATION: (31)..(31)
<223> OTHER INFORMATION: /replace="Val" or "Ser" or "Asp"
<220> FEATURE:
<221> NAME/KEY: MISC_FEATURE
<222> LOCATION: (1)..(107)
<223> OTHER INFORMATION: /note="Variant residues given in the sequence
      have no preference with respect to those in the annotations
      for variant positions"

<400> SEQUENCE: 3
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60
```

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys
            100                 105

<210> SEQ ID NO 4
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (55)..(55)
<223> OTHER INFORMATION: /replace="Glu" or "Ala" or "Gln" or "His" or
      "Asp" or "Lys" or "Arg" or "Ser"
<220> FEATURE:
<221> NAME/KEY: VARIANT
<222> LOCATION: (56)..(56)
<223> OTHER INFORMATION: /replace="Ala"
<220> FEATURE:
<221> NAME/KEY: VARIANT
<222> LOCATION: (102)..(102)
<223> OTHER INFORMATION: /replace="Glu" or "Ser" or "Asn" or "Thr"
<220> FEATURE:
<221> NAME/KEY: VARIANT
<222> LOCATION: (103)..(103)
<223> OTHER INFORMATION: /replace="Ser" or "Ala" or "Thr"
<220> FEATURE:
<221> NAME/KEY: MISC_FEATURE
<222> LOCATION: (1)..(120)
<223> OTHER INFORMATION: /note="Variant residues given in the sequence
      have no preference with respect to those in the annotations
      for variant positions"

<400> SEQUENCE: 4

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Asn Ile Lys Asp Thr
             20                  25                  30

Tyr Ile His Trp Val Arg Gln Ala Pro Gly Lys Gly Leu Glu Trp Val
         35                  40                  45

Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 5
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (56)..(56)
<223> OTHER INFORMATION: Any amino acid except Gly

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Xaa Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 6
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asp Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 7
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
            35                  40                  45

Ala Arg Ile Tyr Pro Thr Glu Gly Tyr Thr Arg Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Ser Phe Tyr Ala Met Asp Tyr Trp Gly Gln
            100                 105                 110

Gly Thr Leu Val Thr Val Ser Ser
            115                 120

<210> SEQ ID NO 8
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 9
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Glu Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

```
Leu Gln Met Asn Ser Leu Arg Ala Glu Asp Thr Ala Val Tyr Tyr Cys
                85                  90                  95

Ser Arg Trp Gly Gly Thr Gly Phe Tyr Ala Met Asp Tyr Trp Gly Gln
            100                 105                 110

Gly Thr Leu Val Thr Val Ser Ser
        115                 120
```

<210> SEQ ID NO 10
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105
```

<210> SEQ ID NO 11
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Ala Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Thr Gly Phe Tyr Ala Met Asp Tyr Trp Gly Gln
            100                 105                 110

Gly Thr Leu Val Thr Val Ser Ser
        115                 120
```

```
<210> SEQ ID NO 12
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 13
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Ser Phe Tyr Ala Met Asp Tyr Trp Gly Gln
            100                 105                 110

Gly Thr Leu Val Thr Val Ser Ser
        115                 120

<210> SEQ ID NO 14
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Thr Thr Ala
            20                  25                  30

Val Ala Trp Tyr Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105
```

```
<210> SEQ ID NO 15
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Ala Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Thr Gly Phe Tyr Ala Met Asp Tyr Trp Gly Gln
            100                 105                 110

Gly Thr Leu Val Thr Val Ser Ser
        115                 120
```

```
<210> SEQ ID NO 16
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Lys Pro Gly Lys Ala Pro Lys Leu Leu Ile
        35                  40                  45
```

```
Tyr Ser Ala Ser Phe Leu Tyr Ser Gly Val Pro Ser Arg Phe Ser Gly
         50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys
                100                 105

<210> SEQ ID NO 17
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Asn Ile Lys Asp Thr
                 20                  25                  30

Tyr Ile His Trp Val Arg Gln Ala Pro Gly Lys Gly Leu Glu Trp Val
             35                  40                  45

Ala Arg Ile Tyr Pro Thr Asn Gly Tyr Thr Arg Tyr Ala Asp Ser Val
         50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Thr Gly Phe Tyr Ala Met Asp Tyr Trp Gly Gln
                100                 105                 110

Gly Thr Leu Val Thr Val Ser Ser
            115                 120

<210> SEQ ID NO 18
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Val Ser Thr Ala
                 20                  25                  30

Val Ala Trp Tyr Gln Gln Lys Pro Gly Lys Ala Pro Lys Leu Leu Ile
             35                  40                  45

Tyr Ser Ala Ser Phe Leu Tyr Ser Gly Val Pro Ser Arg Phe Ser Gly
         50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys
```

100    105

<210> SEQ ID NO 19
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Glu Gly Phe Tyr Ala Met Asp Tyr Trp Gly Gln
            100                 105                 110

Gly Thr Leu Val Thr Val Ser Ser
        115                 120

<210> SEQ ID NO 20
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asp Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 21
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Ala Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Thr Gly Phe Tyr Ala Met Asp Tyr Trp Gly Gln
            100                 105                 110

Gly Thr Leu Val Thr Val Ser Ser
        115                 120

<210> SEQ ID NO 22
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Thr Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 23
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

```
Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
 50                      55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Thr Gly Phe Tyr Ala Met Asp Tyr Trp Gly Gln
                100                 105                 110

Gly Thr Leu Val Thr Val Ser Ser
            115                 120

<210> SEQ ID NO 24
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Ser Thr Ala
             20                  25                  30

Val Ala Trp Tyr Gln Lys Pro Gly Lys Ala Pro Lys Leu Leu Ile
         35                  40                      45

Tyr Ser Ala Ser Phe Leu Tyr Ser Gly Val Pro Ser Arg Phe Ser Gly
 50                      55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys
                100                 105

<210> SEQ ID NO 25
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Asp Thr
             20                  25                  30

Tyr Ile His Trp Val Arg Gln Ala Pro Gly Lys Gly Leu Glu Trp Val
            35                  40                  45

Ala Arg Ile Tyr Pro Thr Asn Ala Tyr Thr Arg Tyr Ala Asp Ser Val
 50                      55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
```

```
                85                  90                  95
Ser Arg Trp Gly Gly Asp Ser Phe Tyr Ala Met Asp Tyr Trp Gly Gln
            100                 105                 110

Gly Thr Leu Val Thr Val Ser Ser
        115                 120

<210> SEQ ID NO 26
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Ala Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 27
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Ala Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Thr Gly Phe Tyr Ala Met Asp Tyr Trp Gly Gln
            100                 105                 110

Gly Thr Leu Val Thr Val Ser
        115
```

<210> SEQ ID NO 28
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Glu Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Ser Phe Tyr Ala Met Asp Tyr Trp Gly Gln
            100                 105                 110

Gly Thr Leu Val Thr Val Ser
        115

<210> SEQ ID NO 29
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Ala Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Ser Phe Tyr Ala Met Asp Tyr Trp Gly Gln
            100                 105                 110

Gly Thr Leu Val Thr Val Ser
        115

<210> SEQ ID NO 30
<211> LENGTH: 119
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic polypeptide"

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Glu Gly Phe Tyr Ala Met Asp Tyr Trp Gly Gln
            100                 105                 110

Gly Thr Leu Val Thr Val Ser
        115

<210> SEQ ID NO 31
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asp Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 32
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
```

```
            20                  25                  30

Tyr Ile His Trp Val Arg Gln Ala Pro Gly Lys Gly Leu Glu Trp Val
            35                  40                  45

Ala Arg Ile Tyr Pro Thr Glu Gly Tyr Thr Arg Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser
        115

<210> SEQ ID NO 33
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Asp Ala
            20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 34
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
            35                  40                  45

Ala Arg Ile Tyr Pro Thr Asn Ala Tyr Thr Arg Tyr Ala Asp Ser Val
        50                  55                  60

Lys Gly Arg Phe Thr Ile Ser Ala Asp Thr Ser Lys Asn Thr Ala Tyr
65                  70                  75                  80
```

```
Leu Gln Met Asn Ser Leu Arg Ala Glu Asp Thr Ala Val Tyr Tyr Cys
                85                  90                  95

Ser Arg Trp Gly Gly Glu Gly Phe Tyr Ala Met Asp Tyr Trp Gly Gln
            100                 105                 110

Gly Thr Leu Val Thr Val Ser
        115
```

<210> SEQ ID NO 35
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 35

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Glu Gly Phe Tyr Ala Met Asp Tyr Trp Gly Gln
            100                 105                 110

Gly Thr Leu Val Thr Val Ser
        115
```

<210> SEQ ID NO 36
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 36

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Asp Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105
```

<210> SEQ ID NO 37
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 37

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Glu Gly Phe Tyr Ala Met Asp Tyr Trp Gly Gln
           100                 105                 110

Gly Thr Leu Val Thr Val Ser
           115
```

<210> SEQ ID NO 38
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 38

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Gln Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
           100                 105
```

<210> SEQ ID NO 39
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

```
<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Ser Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Ser Gly Phe Tyr Ala Met Asp Tyr Trp Gly Gln
            100                 105                 110

Gly Thr Leu Val Thr Val Ser
        115

<210> SEQ ID NO 40
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Ala Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser
        115

<210> SEQ ID NO 41
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Thr Thr Ala
            20                  25                  30
```

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 42
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Thr Thr Ala
            20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 43
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
            35                  40                  45

Ala Arg Ile Tyr Pro Thr Ser Gly Tyr Thr Arg Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Thr Phe Tyr Ala Met Asp Tyr Trp Gly Gln
            100                 105                 110

Gly Thr Leu Val Thr Val Ser
        115

<210> SEQ ID NO 44
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Glu Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 45
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Ser Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser
        115

<210> SEQ ID NO 46
<211> LENGTH: 119
<212> TYPE: PRT

<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Ala Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Thr Phe Tyr Ala Met Asp Tyr Trp Gly Gln
            100                 105                 110

Gly Thr Leu Val Thr Val Ser
        115
```

<210> SEQ ID NO 47
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

```
Arg Ala Ser Gln Asp Val Asn Thr Ala Val Ala
1               5                   10
```

<210> SEQ ID NO 48
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

```
Ser Ala Ser Phe Leu Tyr Ser
1               5
```

<210> SEQ ID NO 49
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

```
Gln Gln His Tyr Thr Thr Pro Pro Thr
1               5
```

<210> SEQ ID NO 50

```
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Asp Thr Tyr Ile His
1               5

<210> SEQ ID NO 51
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Arg Ile Tyr Pro Thr Asn Gly Tyr Thr Arg Tyr Ala Asp Ser Val Lys
1               5                   10                  15

Gly

<210> SEQ ID NO 52
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Trp Gly Gly Asp Gly Phe Tyr Ala Met Asp Tyr
1               5                   10

<210> SEQ ID NO 53
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Arg Ala Ser Gln Asp Val Asp Thr Ala Val Ala
1               5                   10

<210> SEQ ID NO 54
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Arg Ala Ser Gln Asp Val Ser Thr Ala Val Ala
1               5                   10

<210> SEQ ID NO 55
<211> LENGTH: 11
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Arg Ala Ser Gln Asp Val Thr Thr Ala Val Ala
1               5                   10

<210> SEQ ID NO 56
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Arg Ala Ser Gln Asp Val Gln Thr Ala Val Ala
1               5                   10

<210> SEQ ID NO 57
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Arg Ile Tyr Pro Thr Glu Gly Tyr Thr Arg Tyr Ala Asp Ser Val Lys
1               5                   10                  15

Gly

<210> SEQ ID NO 58
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Arg Ile Tyr Pro Thr Asn Ala Tyr Thr Arg Tyr Ala Asp Ser Val Lys
1               5                   10                  15

Gly

<210> SEQ ID NO 59
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Arg Ile Tyr Pro Thr Glu Gly Tyr Thr Arg Tyr Ala Asp Ser Val Lys
1               5                   10                  15

Gly

<210> SEQ ID NO 60
```

```
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Arg Ile Tyr Pro Thr Ala Gly Tyr Thr Arg Tyr Ala Asp Ser Val Lys
1               5                   10                  15

Gly

<210> SEQ ID NO 61
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Arg Ile Tyr Pro Thr Ser Gly Tyr Thr Arg Tyr Ala Asp Ser Val Lys
1               5                   10                  15

Gly

<210> SEQ ID NO 62
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Trp Gly Gly Asp Ser Phe Tyr Ala Met Asp Tyr
1               5                   10

<210> SEQ ID NO 63
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Trp Gly Gly Thr Gly Phe Tyr Ala Met Asp Tyr
1               5                   10

<210> SEQ ID NO 64
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Trp Gly Gly Ser Gly Phe Tyr Ala Met Asp Tyr
1               5                   10

<210> SEQ ID NO 65
```

```
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Arg Trp Gly Gly Glu Gly Phe Tyr Ala Met Asp Tyr
1               5                   10

<210> SEQ ID NO 66
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66

Asn Tyr Tyr Ile His
1               5

<210> SEQ ID NO 67
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 67

Trp Ile Tyr Pro Gly Asp Gly Asn Thr Lys Tyr Asn Glu Lys Phe Lys
1               5                   10                  15

Gly

<210> SEQ ID NO 68
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 68

Asp Ser Tyr Ser Asn Tyr Tyr Phe Asp Tyr
1               5                   10

<210> SEQ ID NO 69
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 69

Lys Ser Ser Gln Ser Leu Leu Asn Ser Arg Thr Arg Lys Asn Tyr Leu
1               5                   10                  15

Ala

<210> SEQ ID NO 70
```

```
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 70

Trp Ala Ser Thr Arg Glu Ser
1               5

<210> SEQ ID NO 71
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

Thr Gln Ser Phe Ile Leu Arg Thr
1               5

<210> SEQ ID NO 72
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 72

Ser Tyr Tyr Ile His
1               5

<210> SEQ ID NO 73
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 73

Trp Ile Tyr Pro Glu Asn Asp Asn Thr Lys Tyr Asn Glu Lys Phe Lys
1               5                   10                  15

Asp

<210> SEQ ID NO 74
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 74

Asp Gly Tyr Ser Arg Tyr Tyr Phe Asp Tyr
1               5                   10

<210> SEQ ID NO 75
<211> LENGTH: 7
<212> TYPE: PRT
```

<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 75

Trp Thr Ser Thr Arg Lys Ser
1               5

<210> SEQ ID NO 76
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 76

Lys Gln Ser Phe Ile Leu Arg Thr
1               5

<210> SEQ ID NO 77
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 77

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile His Trp Val Arg Gln Ala Pro Gly Gln Gly Leu Glu Trp Ile
        35                  40                  45

Gly Trp Ile Tyr Pro Gly Asp Gly Asn Thr Lys Tyr Asn Glu Lys Phe
    50                  55                  60

Lys Gly Arg Ala Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Ser Tyr Ser Asn Tyr Tyr Phe Asp Tyr Trp Gly Gln Gly
            100                 105                 110

Thr Leu Val Thr Val Ser Ser
        115

<210> SEQ ID NO 78
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 78

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Thr Gln
            85                  90                  95

Ser Phe Ile Leu Arg Thr Phe Gly Gln Gly Thr Lys Val Glu Ile Lys
            100                 105                 110

<210> SEQ ID NO 79
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 79

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Tyr Ile His Trp Val Arg Gln Ala Pro Gly Gln Gly Leu Glu Trp Ile
            35                  40                  45

Gly Trp Ile Tyr Pro Glu Asn Asp Asn Thr Lys Tyr Asn Glu Lys Phe
 50                  55                  60

Lys Asp Arg Val Thr Ile Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
            85                  90                  95

Ala Arg Asp Gly Tyr Ser Arg Tyr Tyr Phe Asp Tyr Trp Gly Gln Gly
            100                 105                 110

Thr Leu Val Thr Val Ser Ser
            115

<210> SEQ ID NO 80
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 80

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
            35                  40                  45

Ser Pro Lys Leu Leu Ile Tyr Trp Thr Ser Thr Arg Lys Ser Gly Val
 50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Phe Ile Leu Arg Thr Phe Gly Gln Gly Thr Lys Val Glu Ile Lys
            100                 105                 110

<210> SEQ ID NO 81
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 81

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Lys Pro Gly Gln
        35                  40                  45

Ser Pro Lys Leu Leu Ile Tyr Trp Thr Ser Thr Arg Lys Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Thr Gln
                85                  90                  95

Ser Phe Ile Leu Arg Thr Phe Gly Gln Gly Thr Lys Val Glu Ile Lys
            100                 105                 110

<210> SEQ ID NO 82
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 82

Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr
            20                  25

<210> SEQ ID NO 83
<211> LENGTH: 28
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 83

Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr Cys
            20                  25

<210> SEQ ID NO 84
<211> LENGTH: 5
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Ser"
<220> FEATURE:
<221> NAME/KEY: MISC_FEATURE
<222> LOCATION: (1)..(5)
<223> OTHER INFORMATION: /note="Variant residues given in the sequence
      have no preference with respect to those in the annotations
      for variant positions"

<400> SEQUENCE: 84

Asn Tyr Tyr Ile His
1               5

<210> SEQ ID NO 85
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (5)..(5)
<223> OTHER INFORMATION: /replace="Glu"
<220> FEATURE:
<221> NAME/KEY: VARIANT
<222> LOCATION: (6)..(6)
<223> OTHER INFORMATION: /replace="Asn"
<220> FEATURE:
<221> NAME/KEY: VARIANT
<222> LOCATION: (7)..(7)
<223> OTHER INFORMATION: /replace="Gly"
<220> FEATURE:
<221> NAME/KEY: VARIANT
<222> LOCATION: (17)..(17)
<223> OTHER INFORMATION: /replace="Gly"
<220> FEATURE:
<221> NAME/KEY: MISC_FEATURE
<222> LOCATION: (1)..(17)
<223> OTHER INFORMATION: /note="Variant residue given in the sequence
      has no preference with respect to that in the annotations
      for variant position"

<400> SEQUENCE: 85

Trp Ile Tyr Pro Gly Asp Asp Asn Thr Lys Tyr Asn Glu Lys Phe Lys
1               5                   10                  15

Asp

<210> SEQ ID NO 86
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(2)
<223> OTHER INFORMATION: /replace="Gly"
<220> FEATURE:
<221> NAME/KEY: VARIANT
<222> LOCATION: (5)..(5)
<223> OTHER INFORMATION: /replace="Arg"
<220> FEATURE:
<221> NAME/KEY: MISC_FEATURE
```

```
<222> LOCATION: (1)..(10)
<223> OTHER INFORMATION: /note="Variant residue given in the sequence
      has no preference with respect to that in the annotations
      for variant position"

<400> SEQUENCE: 86

Asp Ser Tyr Ser Asn Tyr Tyr Phe Asp Tyr
1               5                   10

<210> SEQ ID NO 87
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(2)
<223> OTHER INFORMATION: /replace="Thr"
<220> FEATURE:
<221> NAME/KEY: VARIANT
<222> LOCATION: (6)..(6)
<223> OTHER INFORMATION: /replace="Lys"
<220> FEATURE:
<221> NAME/KEY: MISC_FEATURE
<222> LOCATION: (1)..(7)
<223> OTHER INFORMATION: /note="Variant residue given in the sequence
      has no preference with respect to that in the annotations
      for variant position"

<400> SEQUENCE: 87

Trp Ala Ser Thr Arg Glu Ser
1               5

<210> SEQ ID NO 88
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Thr"
<220> FEATURE:
<221> NAME/KEY: MISC_FEATURE
<222> LOCATION: (1)..(8)
<223> OTHER INFORMATION: /note="Variant residue given in the sequence
      has no preference with respect to that in the annotations
      for variant position"

<400> SEQUENCE: 88

Lys Gln Ser Phe Ile Leu Arg Thr
1               5

<210> SEQ ID NO 89
<211> LENGTH: 16
<212> TYPE: PRT
<213> ORGANISM: Homo sapiens

<400> SEQUENCE: 89

Gln Asp Gly Asn Glu Glu Met Gly Gly Ile Thr Gln Thr Pro Tyr Lys
1               5                   10                  15
```

What is claimed is:

1. An isolated anti-HER2 antibody comprising a HER2 binding domain comprising
   i. (a) an HVR-H1 comprising the amino acid sequence of SEQ ID NO:50; (b) an HVR-H2 comprising the amino acid sequence of SEQ ID NO:57; (c) an HVR-H3 comprising the amino acid sequence of SEQ ID NO:62; (d) an HVR-L1 comprising the amino acid sequence of SEQ ID NO: 53; (e) an HVR-L2 comprising the amino acid sequence of SEQ ID NO:48; and (f) an HVR-L3 comprising the amino acid sequence of SEQ ID NO:49; or
   ii. (a) an HVR-H1 comprising the amino acid sequence of SEQ ID NO:50; (b) an HVR-H2 comprising the amino acid sequence of SEQ ID NO:57; (c) an HVR-H3 comprising the amino acid sequence of SEQ ID NO:63; (d) an HVR-L1 comprising the amino acid sequence of SEQ ID NO: 54; (e) an HVR-L2 comprising the amino acid sequence of SEQ ID NO:48; and (f) an HVR-L3 comprising the amino acid sequence of SEQ ID NO:49; or
   iii. (a) an HVR-H1 comprising the amino acid sequence of SEQ ID NO:50; (b) an HVR-H2 comprising the amino acid sequence of SEQ ID NO:58; (c) an HVR-H3 comprising the amino acid sequence of SEQ ID NO:63; (d) an HVR-L1 comprising the amino acid sequence of SEQ ID NO: 54; (e) an HVR-L2 comprising the amino acid sequence of SEQ ID NO:48; and (f) an HVR-L3 comprising the amino acid sequence of SEQ ID NO:49; or
   iv. (a) an HVR-H1 comprising the amino acid sequence of SEQ ID NO:50; (b) an HVR-H2 comprising the amino acid sequence of SEQ ID NO:51; (c) an HVR-H3 comprising the amino acid sequence of SEQ ID NO:62; (d) an HVR-L1 comprising the amino acid sequence of SEQ ID NO: 54; (e) an HVR-L2 comprising the amino acid sequence of SEQ ID NO:48; and (f) an HVR-L3 comprising the amino acid sequence of SEQ ID NO:49; or
   v. (a) an HVR-H1 comprising the amino acid sequence of SEQ ID NO:50; (b) an HVR-H2 comprising the amino acid sequence of SEQ ID NO:58; (c) an HVR-H3 comprising the amino acid sequence of SEQ ID NO:63; (d) an HVR-L1 comprising the amino acid sequence of SEQ ID NO: 55; (e) an HVR-L2 comprising the amino acid sequence of SEQ ID NO:48; and (f) an HVR-L3 comprising the amino acid sequence of SEQ ID NO:49; or
   vi. (a) an HVR-H1 comprising the amino acid sequence of SEQ ID NO:50; (b) an HVR-H2 comprising the amino acid sequence of SEQ ID NO:51; (c) an HVR-H3 comprising the amino acid sequence of SEQ ID NO:63; (d) an HVR-L1 comprising the amino acid sequence of SEQ ID NO: 54; (e) an HVR-L2 comprising the amino acid sequence of SEQ ID NO:48; and (f) an HVR-L3 comprising the amino acid sequence of SEQ ID NO:49; or
   vii. (a) an HVR-H1 comprising the amino acid sequence of SEQ ID NO:50; (b) an HVR-H2 comprising the amino acid sequence of SEQ ID NO:51; (c) an HVR-H3 comprising the amino acid sequence of SEQ ID NO:65; (d) an HVR-L1 comprising the amino acid sequence of SEQ ID NO:54; (e) an HVR-L2 comprising the amino acid sequence of SEQ ID NO:48; and (f) an HVR-L3 comprising the amino acid sequence of SEQ ID NO:49;
   viii. (a) an HVR-H1 comprising the amino acid sequence of SEQ ID NO:50; (b) an HVR-H2 comprising the amino acid sequence of SEQ ID NO:58; (c) an HVR-H3 comprising the amino acid sequence of SEQ ID NO:63; (d) an HVR-L1 comprising the amino acid sequence of SEQ ID NO:53; (e) an HVR-L2 comprising the amino acid sequence of SEQ ID NO:48; and (f) an HVR-L3 comprising the amino acid sequence of SEQ ID NO:49; or
   ix. (a) an HVR-H1 comprising the amino acid sequence of SEQ ID NO:50; (b) an HVR-H2 comprising the amino acid sequence of SEQ ID NO:51; (c) an HVR-H3 comprising the amino acid sequence of SEQ ID NO:63; (d) an HVR-L1 comprising the amino acid sequence of SEQ ID NO:55; (e) an HVR-L2 comprising the amino acid sequence of SEQ ID NO:48; and (f) an HVR-L3 comprising the amino acid sequence of SEQ ID NO:49.

2. An isolated anti-HER2 antibody comprising a light chain variable domain (VL) comprising the amino acid sequence of SEQ ID NO: 3 and a heavy chain variable domain (VH) comprising the amino acid sequence of SEQ ID NO: 4.

3. An isolated anti-HER2 antibody comprising a light chain variable domain (VL) comprising the amino acid sequence of SEQ ID NO: 3 and a heavy chain variable domain (VH) comprising the amino acid sequence of SEQ ID NO: 5.

4. The anti-HER2 antibody of claim 1, comprising a HER2 binding domain comprising:
   i. a light chain variable domain (VL) comprising the amino acid sequence of SEQ ID NO: 6 and a heavy chain variable domain (VH) comprising the amino acid sequence of SEQ ID NO: 7; or
   ii. a light chain variable domain (VL) comprising the amino acid sequence of SEQ ID NO: 8 and a heavy chain variable domain (VH) comprising the amino acid sequence of SEQ ID NO: 9; or
   iii. a light chain variable domain (VL) comprising the amino acid sequence of SEQ ID NO: 10 and a heavy chain variable domain (VH) comprising the amino acid sequence of SEQ ID NO: 11; or
   iv. a light chain variable domain (VL) comprising the amino acid sequence of SEQ ID NO: 12 and a heavy chain variable domain (VH) comprising the amino acid sequence of SEQ ID NO: 13; or
   v. a light chain variable domain (VL) comprising the amino acid sequence of SEQ ID NO: 14 and a heavy chain variable domain (VH) comprising the amino acid sequence of SEQ ID NO: 15; or
   vi. a light chain variable domain (VL) comprising the amino acid sequence of SEQ ID NO: 16 and a heavy chain variable domain (VH) comprising the amino acid sequence of SEQ ID NO: 17; or
   vii. a light chain variable domain (VL) comprising the amino acid sequence of SEQ ID NO: 18 and a heavy chain variable domain (VH) comprising the amino acid sequence of SEQ ID NO: 19; or
   viii. a light chain variable domain (VL) comprising the amino acid sequence of SEQ ID NO: 20 and a heavy chain variable domain (VH) comprising the amino acid sequence of SEQ ID NO: 21; or
   ix. a light chain variable domain (VL) comprising the amino acid sequence of SEQ ID NO: 22 and a heavy chain variable domain (VH) comprising the amino acid sequence of SEQ ID NO: 23.

5. The anti-HER2 antibody of claim 1, wherein the anti-HER2 antibody further comprises an anti-CD3 binding domain.

6. The anti-HER2 antibody of claim 5, wherein the anti-CD3 binding domain comprises:
   i. (a) HVR-H1 comprising the amino acid sequence of SEQ ID NO:84 (b) HVR-H2 comprising the amino acid sequence of SEQ ID NO:85; (c) HVR-H3 comprising the amino acid sequence of SEQ ID NO:86; (d) HVR-L1 comprising the amino acid sequence of SEQ ID NO:69; (e) HVR-L2 comprising the amino acid sequence of SEQ ID NO:87, and (f) HVR-L3 comprising the amino acid sequence of SEQ ID NO:88; or
   ii. (a) HVR-H1 comprising the amino acid sequence of SEQ ID NO:66; (b) HVR-H2 comprising the amino acid sequence of SEQ ID NO:67; (c) HVR-H3 comprising the amino acid sequence of SEQ ID NO:68; (d) HVR-L1 comprising the amino acid sequence of SEQ ID NO:69; (e) HVR-L2 comprising the amino acid sequence of SEQ ID NO:70, and (f) HVR-L3 comprising the amino acid sequence of SEQ ID NO:71; or
   iii. a VH domain comprising the amino acid sequence of SEQ ID NO:77 and a VL domain comprising the amino acid sequence of SEQ ID NO:78; or
   iv. (a) HVR-H1 comprising the amino acid sequence of SEQ ID NO:72; (b) HVR-H2 comprising the amino acid sequence of SEQ ID NO:73; (c) HVR-H3 comprising the amino acid sequence of SEQ ID NO:74; (d) HVR-L1 comprising the amino acid sequence of SEQ ID NO:69; (e) HVR-L2 comprising the amino acid sequence of SEQ ID NO:75; and (f) HVR-L3 comprising the amino acid sequence of SEQ ID NO:76; or
   v. a VH domain comprising the amino acid sequence of SEQ ID NO:79 and a VL domain comprising the amino acid sequence of SEQ ID NO:81.

7. The anti-HER2 antibody of claim 1, wherein the anti-HER2 antibody is a monoclonal, humanized, or chimeric antibody.

8. The anti-HER2 antibody of claim 1, wherein the anti-HER2 antibody is an IgG antibody.

9. The anti-HER2 antibody of claim 1, wherein the anti-HER2 antibody is a multispecific antibody.

10. The anti-HER2 antibody of claim 1, wherein the anti-HER2 antibody is a full-length antibody.

11. The anti-HER2 antibody of claim 1, wherein the anti-HER2 antibody comprises an aglycosylation site mutation.

12. The anti-HER2 antibody of claim 1, wherein the aglycosylation site mutation is a substitution mutation.

13. The anti-HER2 antibody of claim 1, wherein the anti-HER2 antibody has reduced effector function.

14. The anti-HER2 antibody of claim 1, wherein the anti-HER2 antibody comprises a substitution mutation is at amino acid residue N297, L234, L235, D265, and/or P329G according to EU numbering.

15. The anti-HER2 antibody of claim 14, wherein the substitution mutation is selected from the group consisting of N297G, N297A, L234A, L235A, D265A, and P329G according to EU numbering.

16. The anti-HER2 antibody of claim 15, wherein the anti-HER2 antibody comprises an N297G substitution mutation at amino acid residue 297 according to EU numbering.

17. The anti-HER2 antibody of claim 1, wherein the anti-HER2 antibody is an antibody fragment.

18. The anti-HER2 antibody of claim 17, wherein the antibody fragment is selected from the group consisting of a Fab, Fab'-SH, Fv, scFv, and a (Fab')2 fragment.

19. An isolated nucleic acid encoding the anti-HER2 antibody of claim 1.

20. A vector comprising the isolated nucleic acid of claim 19.

21. A host cell comprising the vector of claim 20.

22. A method of producing the anti-HER2 antibody of claim 1, the method comprising culturing the host cell of claim 21 in a culture medium.

23. A pharmaceutical composition comprising the anti-HER2 antibody of claim 1.

24. A method of treating or delaying the progression of a cell proliferative disorder in a subject in need thereof, the method comprising administering to the subject the anti-HER2 antibody of claim 1.

25. A method of enhancing immune function in a subject having a cell proliferative disorder, the method comprising administering to the subject an effective amount of the anti-HER2 antibody of claim 1.

26. The method of claim 24 or 25, wherein the cell proliferative disorder is a cancer.

27. The method of claim 26, wherein the cancer expresses HER2.

28. The method of claim 26, wherein the cancer is a HER2 positive cancer.

29. The method of claim 26, wherein the cancer is breast cancer or gastric cancer.

30. The method of claim 26, further comprising administering to the subject a PD-1 axis binding antagonist.

31. An isolated anti-HER2 antibody comprising a HER2 binding domain comprising (a) an HVR-H1 comprising the amino acid sequence of SEQ ID NO:50; (b) an HVR-H2 comprising the amino acid sequence of SEQ ID NO:58; (c) an HVR-H3 comprising the amino acid sequence of SEQ ID NO:63; (d) an HVR-L1 comprising the amino acid sequence of SEQ ID NO: 54; (e) an HVR-L2 comprising the amino acid sequence of SEQ ID NO:48; and (f) an HVR-L3 comprising the amino acid sequence of SEQ ID NO:49.

32. The anti-HER2 antibody of claim 31, wherein the anti-HER2 antibody further comprises an anti-CD3 binding domain comprising (a) an HVR-H1 comprising the amino acid sequence of SEQ ID NO:66; (b) an HVR-H2 comprising the amino acid sequence of SEQ ID NO:67; (c) an HVR-H3 comprising the amino acid sequence of SEQ ID NO:68; (d) an HVR-L1 comprising the amino acid sequence of SEQ ID NO:69; (e) an HVR-L2 comprising the amino acid sequence of SEQ ID NO:70, and (f) an HVR-L3 comprising the amino acid sequence of SEQ ID NO:71.

33. An isolated anti-HER2 antibody comprising a light chain variable domain (VL) comprising the amino acid sequence of SEQ ID NO: 10 and a heavy chain variable domain (VH) comprising the amino acid sequence of SEQ ID NO: 11.

34. The anti-HER2 antibody of claim 33, wherein the anti-HER2 antibody further comprises an anti-CD3 binding domain comprising a light chain variable domain (VL) comprising the amino acid sequence of SEQ ID NO: 77 and a heavy chain variable domain (VH) comprising the amino acid sequence of SEQ ID NO: 78.

35. The anti-HER2 antibody of claim 34, further comprising an N297G substitution mutation at amino acid residue 297 according to EU numbering.

* * * * *